United States Patent
Kim et al.

(10) Patent No.: US 9,532,723 B2
(45) Date of Patent: Jan. 3, 2017

(54) MOBILE TERMINAL AND CONTROLLING METHOD THEREOF

(71) Applicant: LG ELECTRONICS INC., Seoul (KR)

(72) Inventors: Youngsik Kim, Seoul (KR); Hongjo Shim, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 0 days.

(21) Appl. No.: 14/795,796

(22) Filed: Jul. 9, 2015

(65) Prior Publication Data

US 2016/0029899 A1 Feb. 4, 2016

(30) Foreign Application Priority Data

Jul. 31, 2014 (KR) ........................ 10-2014-0098339

(51) Int. Cl.
| | | |
|---|---|---|
| H04M 3/42 | (2006.01) |
| A61B 5/026 | (2006.01) |
| G06F 19/00 | (2011.01) |
| A61B 5/024 | (2006.01) |
| A61B 5/11 | (2006.01) |
| A61B 5/00 | (2006.01) |
| H04M 1/725 | (2006.01) |
| H04W 68/00 | (2009.01) |
| G06F 3/03 | (2006.01) |

(52) U.S. Cl.
CPC .......... *A61B 5/026* (2013.01); *A61B 5/02438* (2013.01); *A61B 5/1118* (2013.01); *A61B 5/4809* (2013.01); *A61B 5/681* (2013.01); *G06F 19/3406* (2013.01); *H04M 1/7253* (2013.01); *H04M 1/72522* (2013.01); *H04W 68/005* (2013.01); *G06F 3/03* (2013.01)

(58) Field of Classification Search
CPC . A61B 5/026; A61B 5/02438; G06F 19/3406; G06F 3/03
USPC ................................................ 455/414.1, 423
See application file for complete search history.

(56) References Cited

U.S. PATENT DOCUMENTS

| | | | |
|---|---|---|---|
| 2009/0174578 A1* | 7/2009 | Taki ..................... | G01B 11/002 341/20 |
| 2013/0138357 A1* | 5/2013 | Watson ............... | A61B 5/14551 702/19 |
| 2014/0135612 A1* | 5/2014 | Yuen ................... | A61B 5/02405 600/407 |
| 2016/0029899 A1* | 2/2016 | Kim .................... | A61B 5/02438 455/414.1 |

FOREIGN PATENT DOCUMENTS

| | | |
|---|---|---|
| EP | 2698686 | 2/2014 |
| WO | 2012-170922 | 12/2012 |

OTHER PUBLICATIONS

European Patent Office Application Serial No. 151785565.5, Search Report dated Dec. 17, 2015, 7 pages.

\* cited by examiner

*Primary Examiner* — Qutbuddin Ghulamali

(74) *Attorney, Agent, or Firm* — Lee, Hong, Degerman, Kang & Waimey

(57) ABSTRACT

A mobile terminal and controlling method thereof are disclosed, by which a function adaptive to a situation can be provided by detecting a blood flow rate in a wrist having a watch type mobile terminal worn thereon. The present invention includes a display, a band configured to be worn on a wrist of a user, a sensing unit configured to measure a blood flow rate in the wrist having the band worn thereon, and a controller controlling the display to display a running screen of a prescribed function if a variation of the measured blood flow rate is generated.

18 Claims, 28 Drawing Sheets

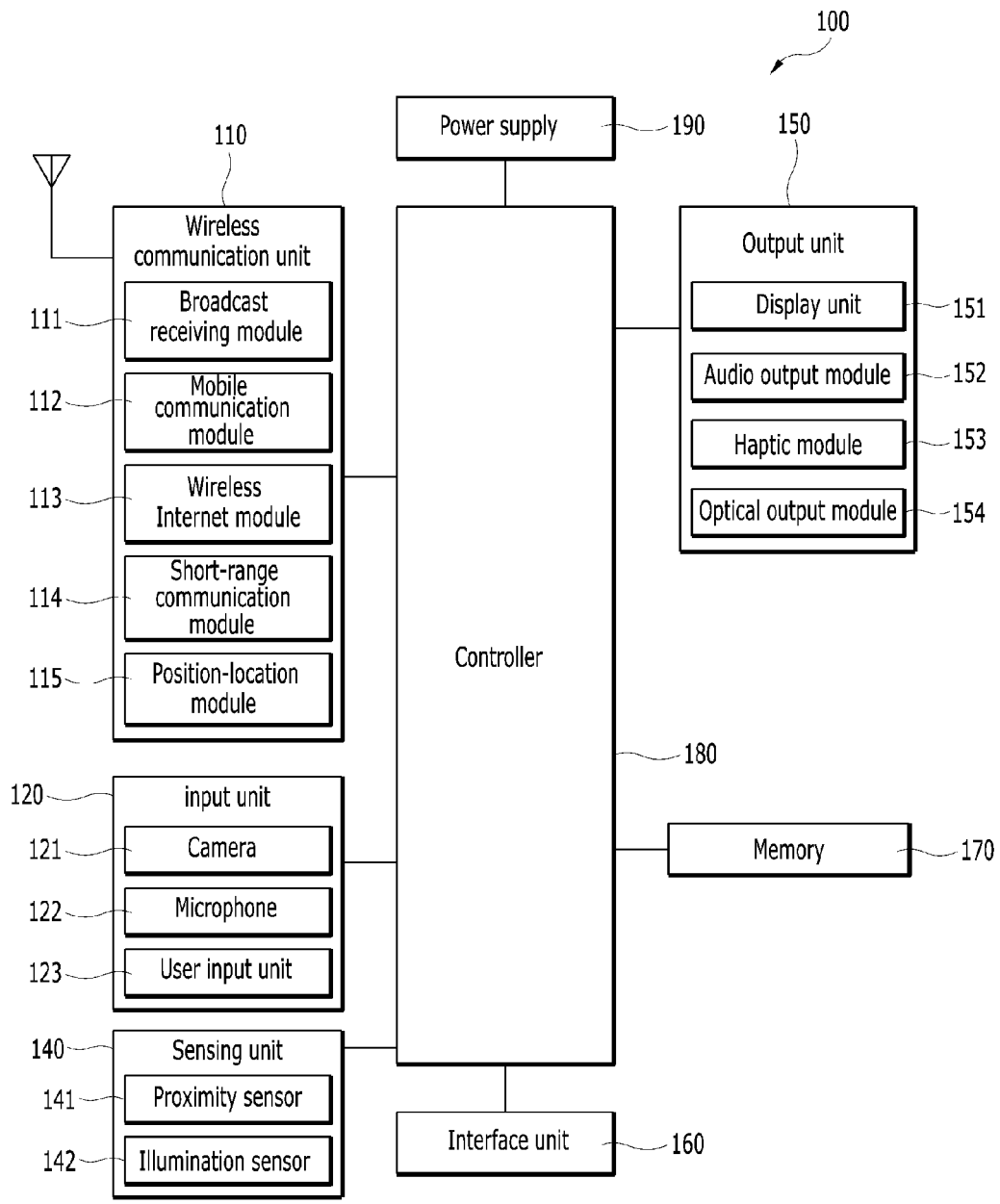

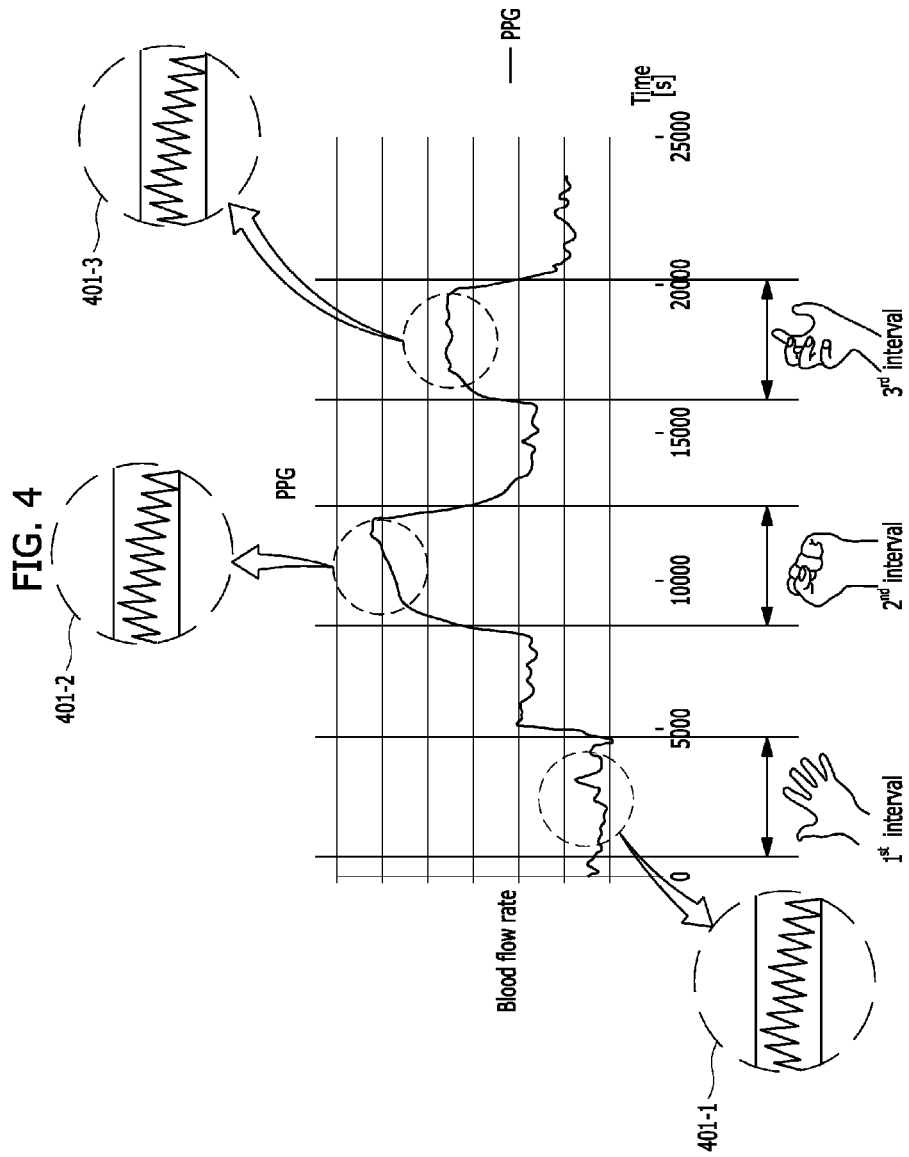

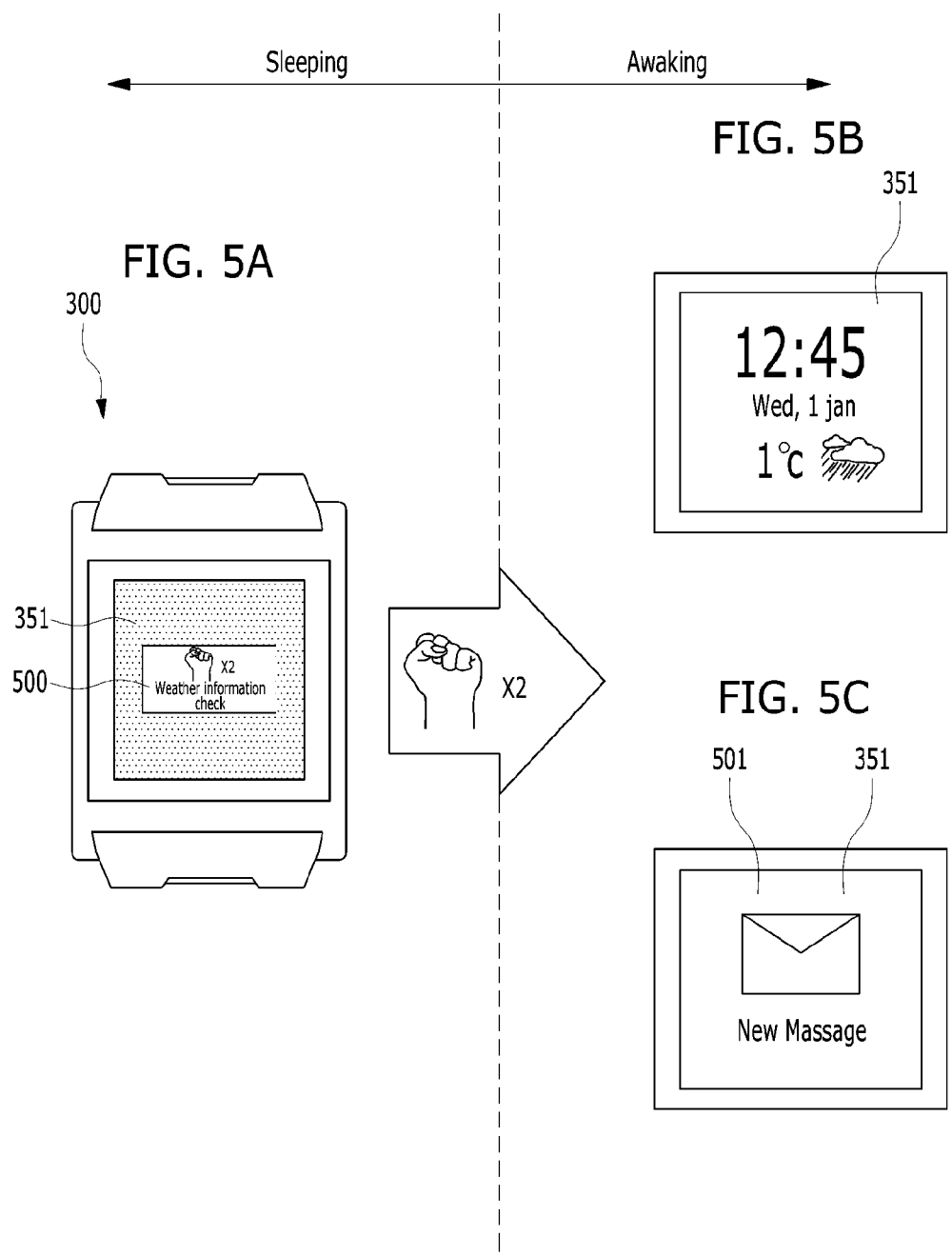

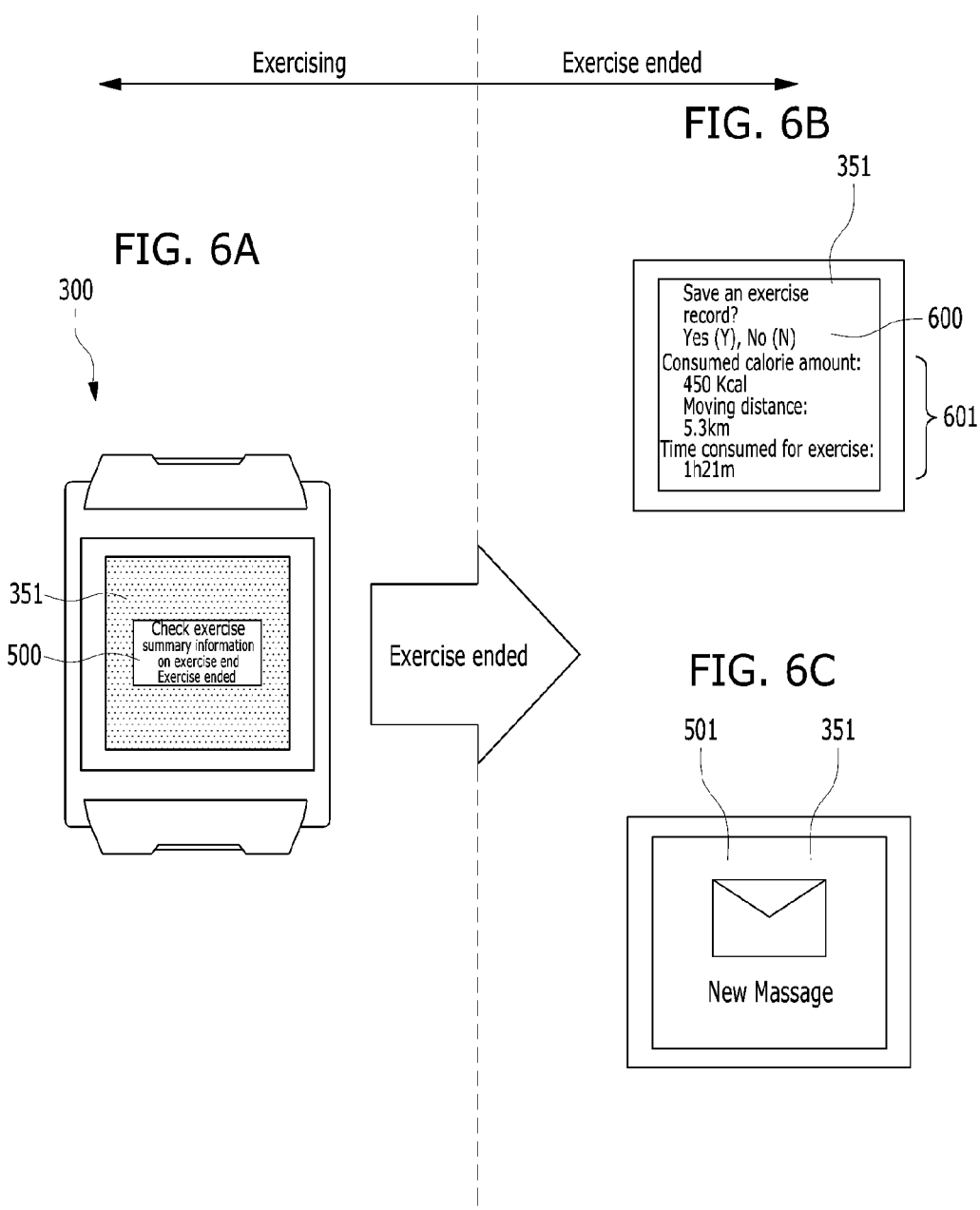

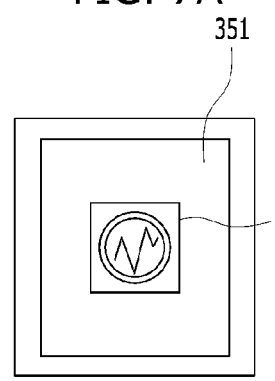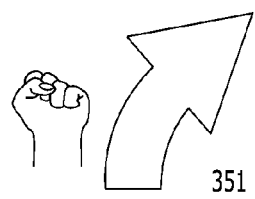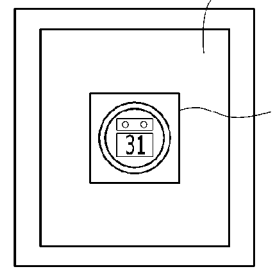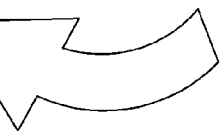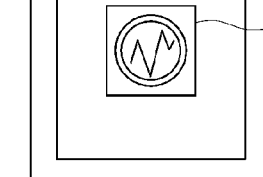

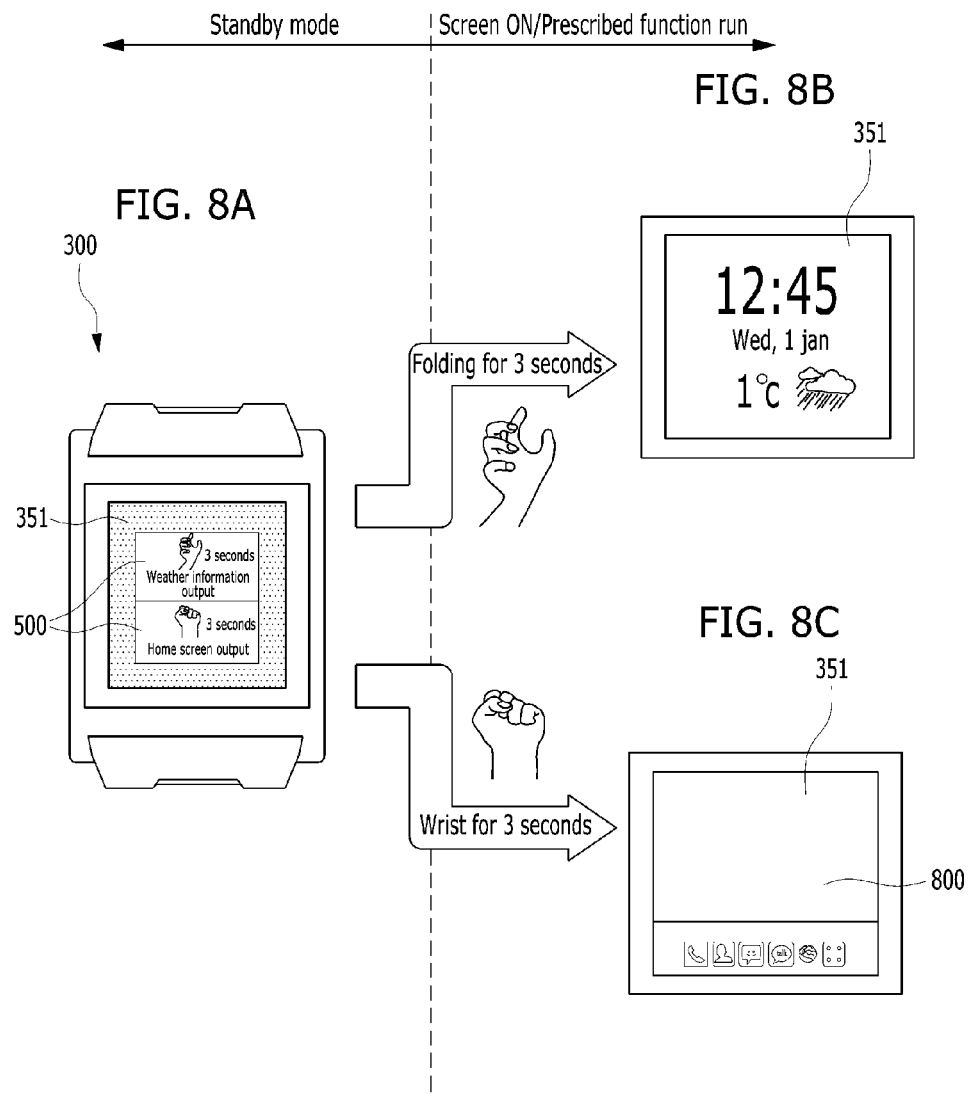

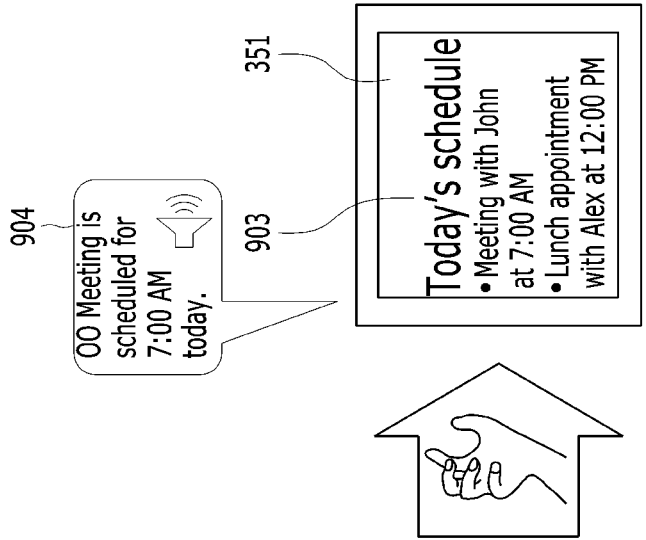
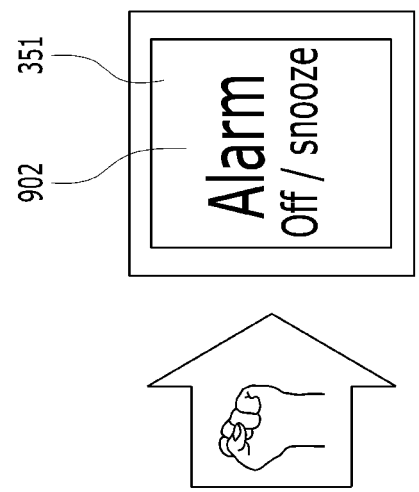
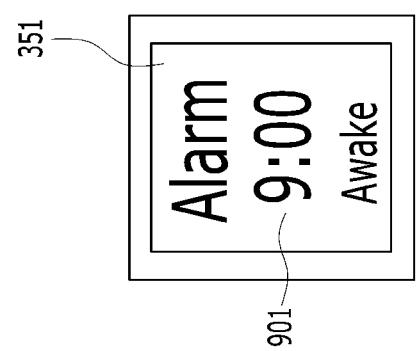

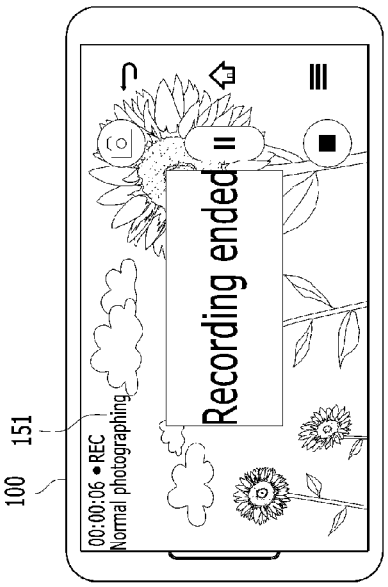
FIG. 10B
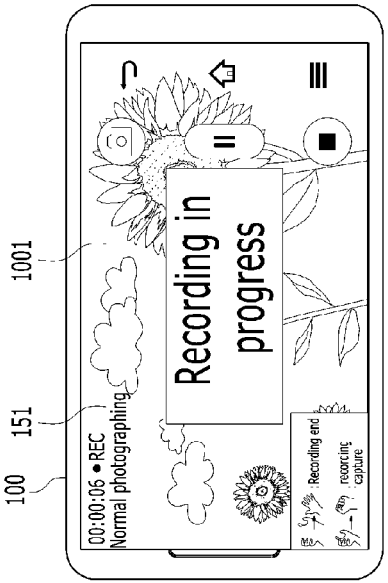
FIG. 10A
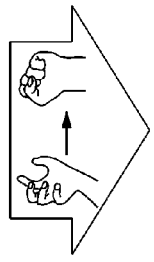
FIG. 10C

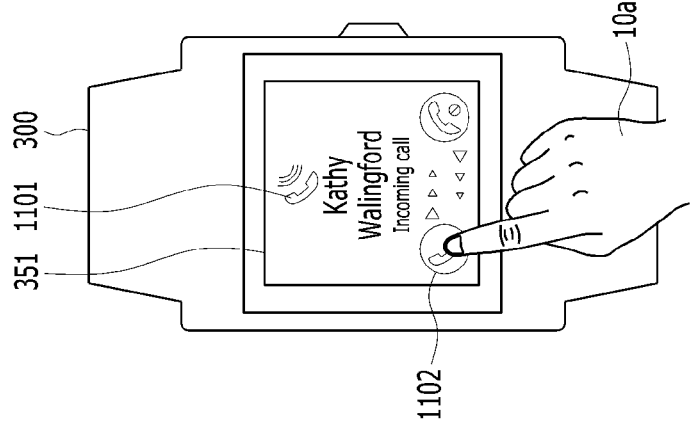
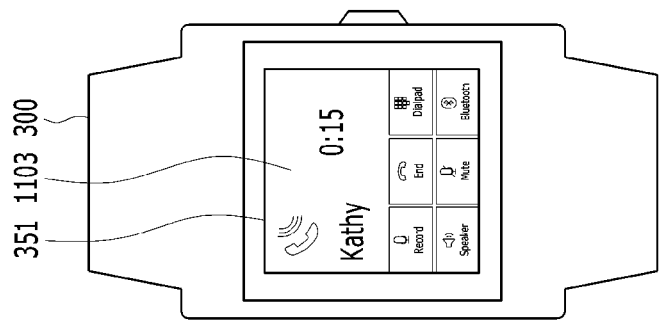
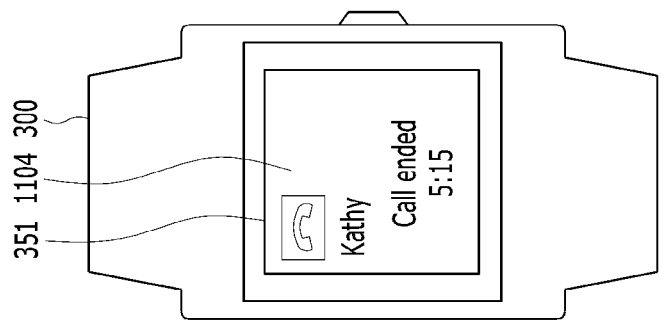

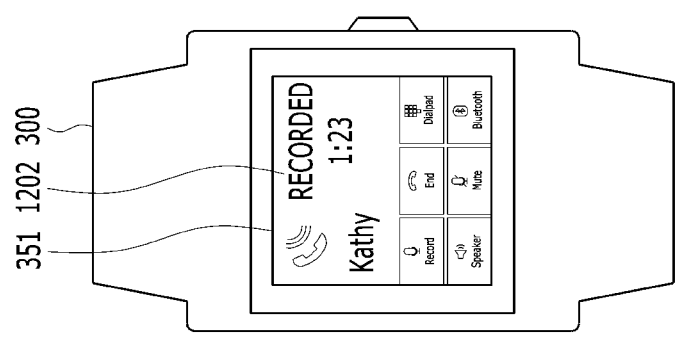
FIG. 12C
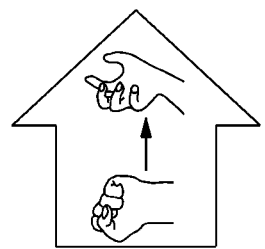
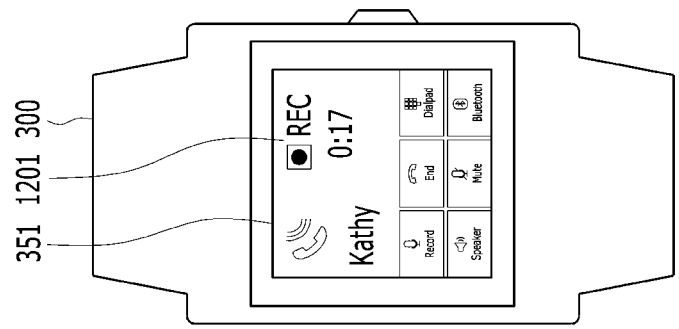
FIG. 12B
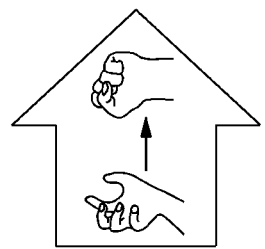
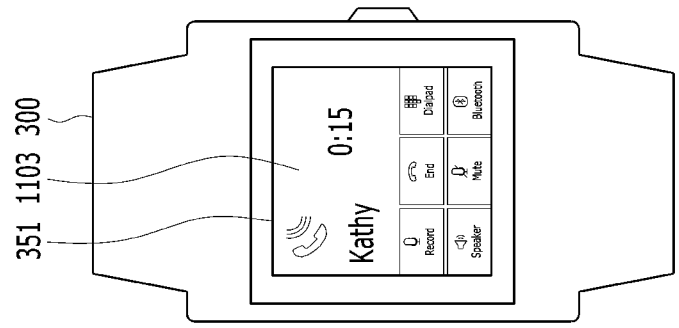
FIG. 12A

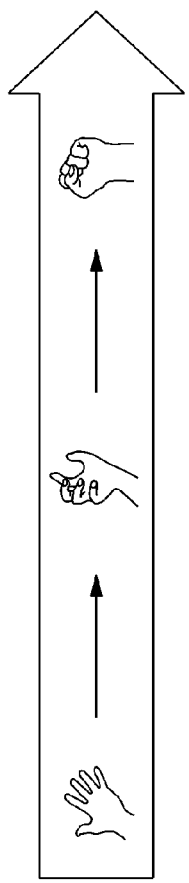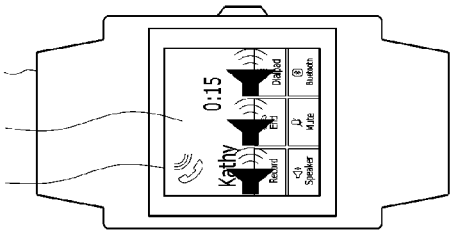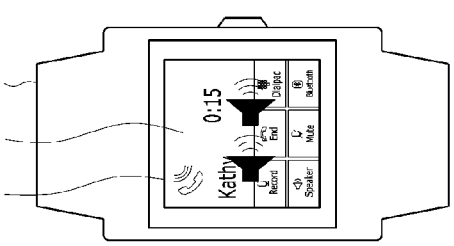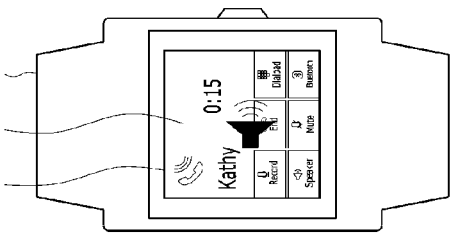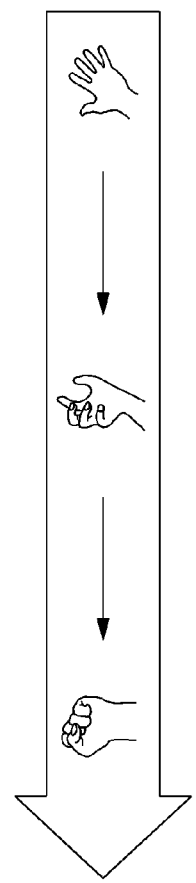

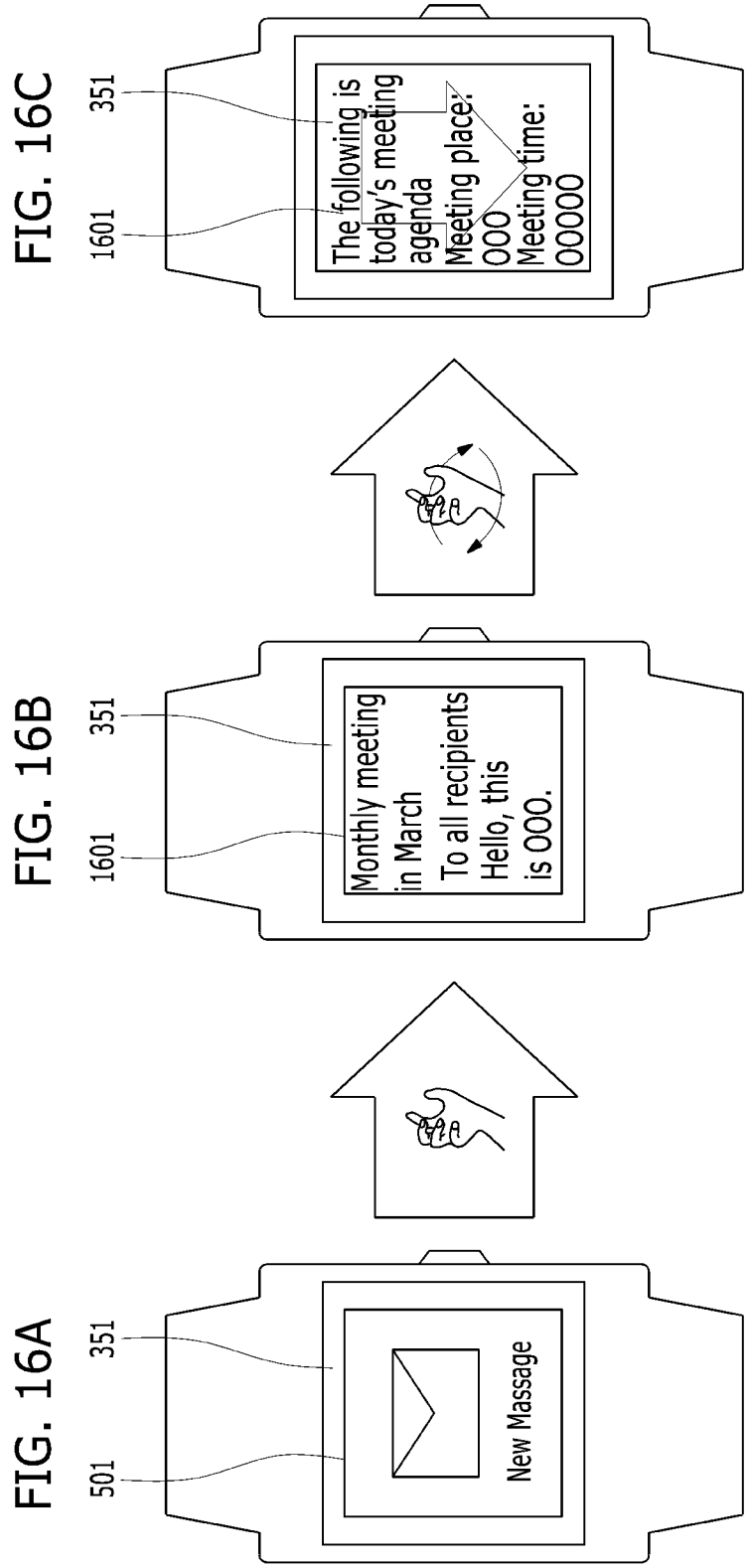

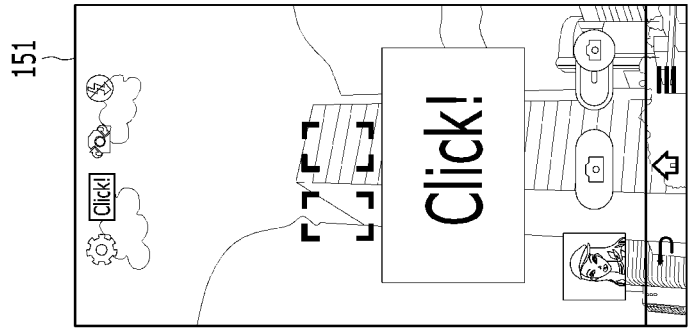
FIG. 19A
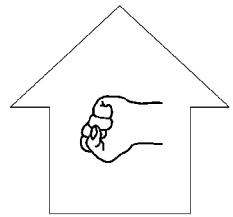
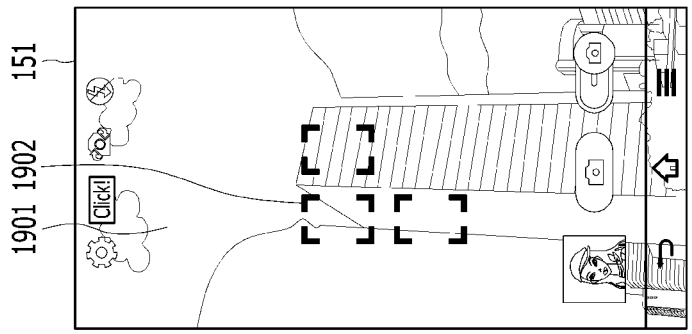
FIG. 19B
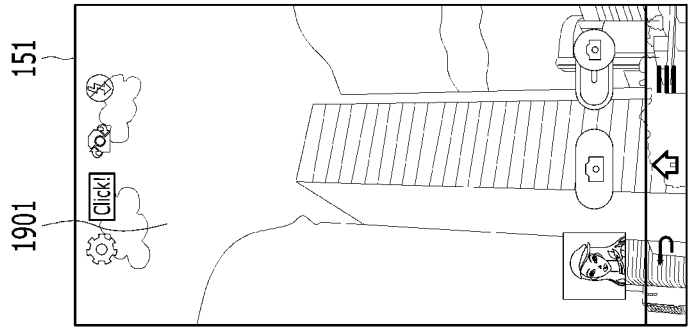
FIG. 19C

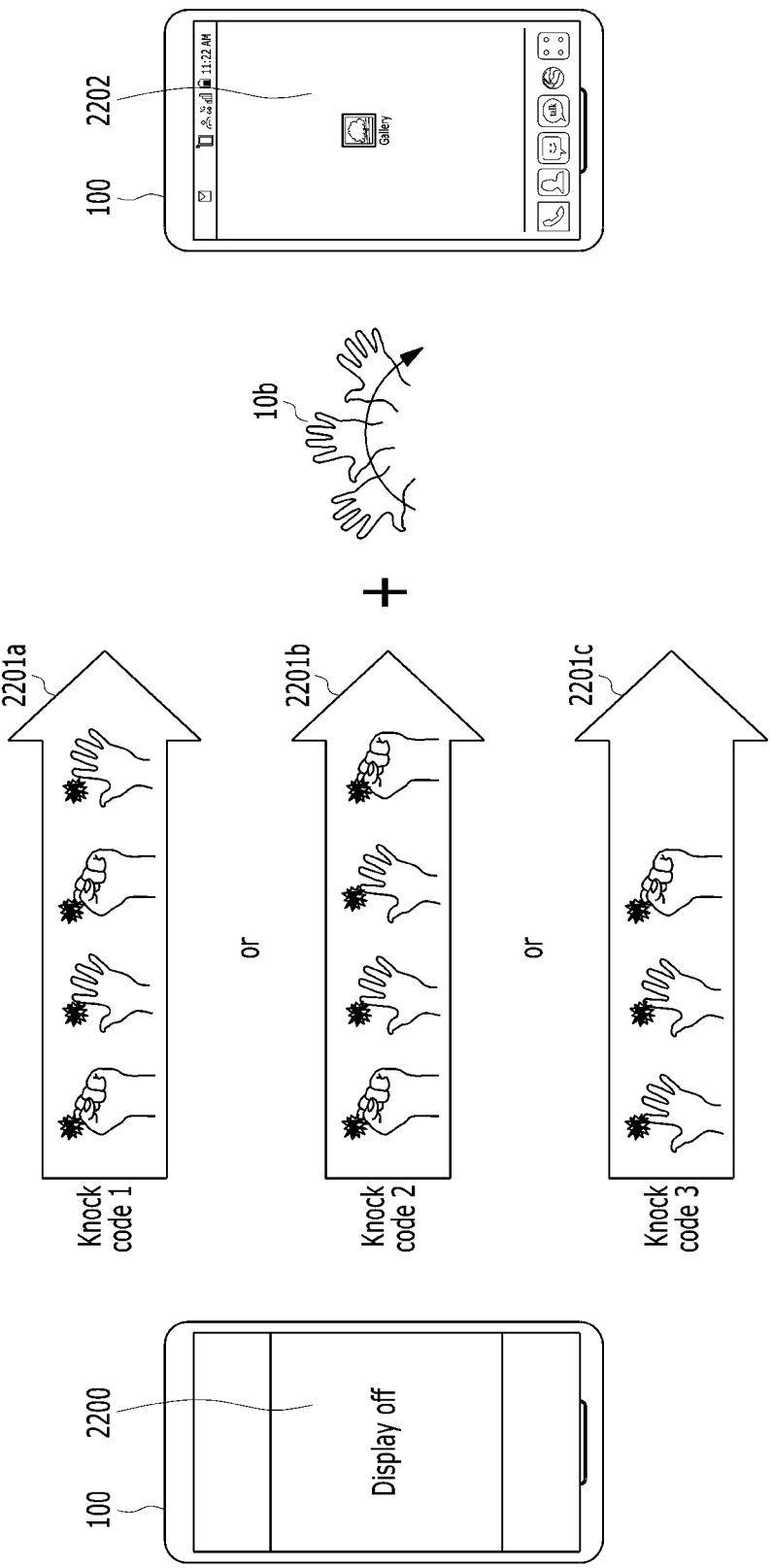

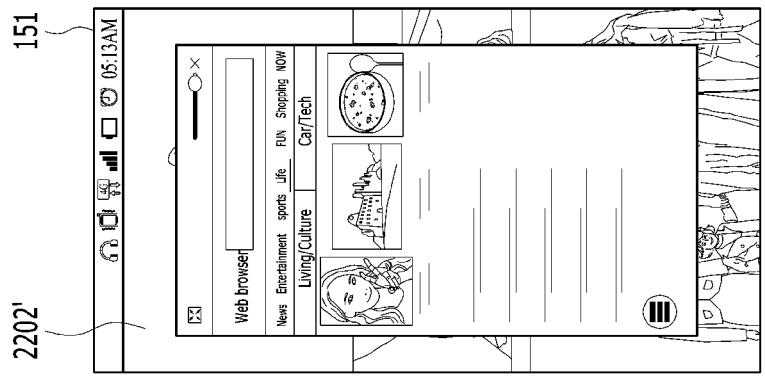
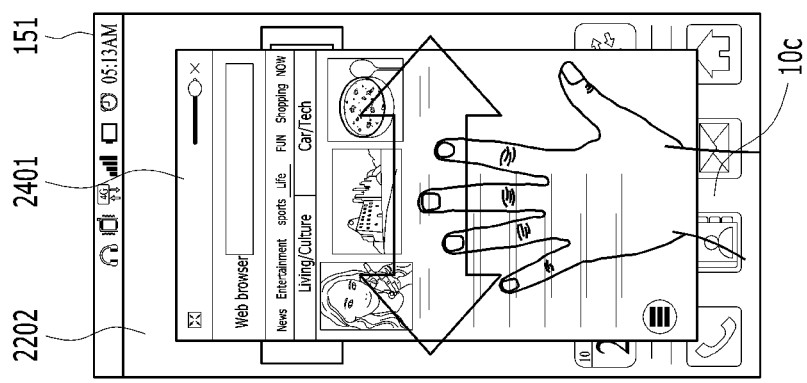

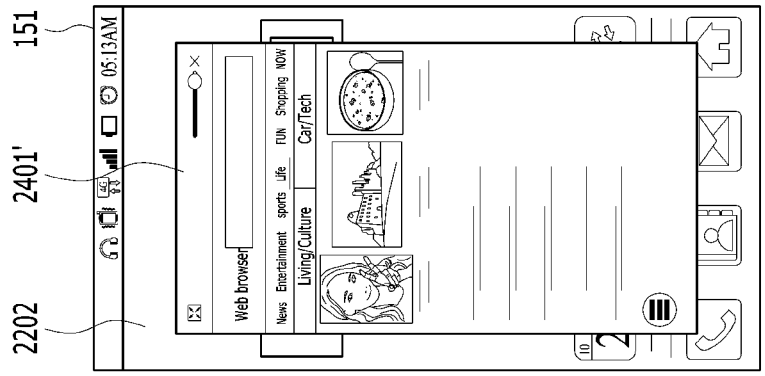
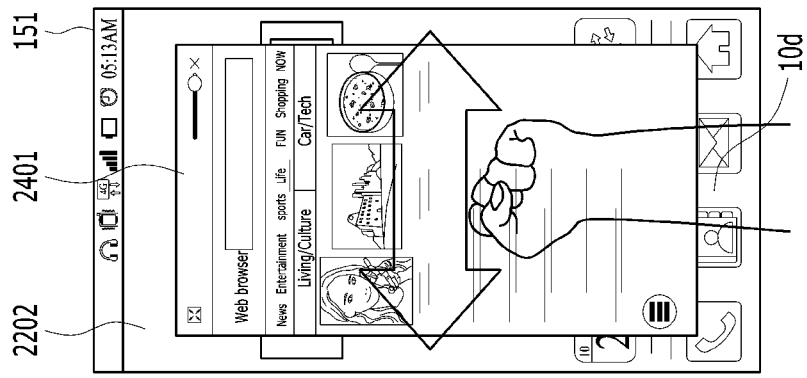

MOBILE TERMINAL AND CONTROLLING METHOD THEREOF

CROSS-REFERENCE TO RELATED APPLICATIONS

Pursuant to 35 U.S.C. §119(a), this application claims the benefit of earlier filing date and right of priority to Korean Patent Application No. 10-2014-0098339, filed on Jul. 31, 2014 the contents of which are all hereby incorporated by reference herein in its entirety.

BACKGROUND OF THE INVENTION

Field of the Invention

The present invention relates to a mobile terminal, and more particularly, to a mobile terminal and controlling method thereof. Although the present invention is suitable for a wide scope of applications, it is particularly suitable for facilitating the use of a terminal in further consideration of user's convenience.

Discussion of the Related Art

A mobile terminal is a device which may be configured to perform various functions. Examples of such functions include data and voice communications, capturing images and video via a camera, recording audio, playing music files and outputting music via a speaker system, and displaying images and video on a display. Some terminals include additional functionality which supports game playing, while other terminals are also configured as multimedia players. More recently, mobile terminals have been configured to receive broadcast and multicast signals which permit viewing of contents, such as videos and television programs.

Generally, terminals can be classified into mobile terminals and stationary terminals according to a presence or non-presence of mobility. And, the mobile terminals can be further classified into handheld terminals and vehicle mount terminals according to availability for hand-carry.

There are ongoing efforts to support and increase the functionality of mobile terminals. Such efforts include software and hardware improvements, as well as changes and improvements in the structural components which form the mobile terminal.

The recent tendency of a mobile terminal market attempts to develop mobile terminals of various types to meet the diversity of the consumer's needs. The types of the developed mobile terminals are focused on the configuration that can emphasize the portability of the mobile terminal. The mobile terminal types for high portability can include such a type wearable on a user's body as a watch type, a glasses type, a necklace type and the like. The mobile terminals of those types exist in case of having difficulty in applying the conventionally used input/output means in the same manner. For instance, since these mobile terminals have a display size relatively smaller than that of a mobile terminal of an existing type, it is necessary to consider a different kind of an output means. Particularly, in case of a mobile terminal of a watch e type, an input means of a totally new type is required due to a limited size of the mobile terminal.

SUMMARY OF THE INVENTION

Accordingly, embodiments of the present invention are directed to a mobile terminal and controlling method thereof that substantially obviate one or more problems due to limitations and disadvantages of the related art.

One object of the present invention is to provide a mobile terminal and controlling method thereof, by which a motion of unfolding and folding fingers can be used as an input means.

Technical tasks obtainable from the present invention are non-limited by the above-mentioned technical tasks. And, other unmentioned technical tasks can be clearly understood from the following description by those having ordinary skill in the technical field to which the present invention pertains.

Additional advantages, objects, and features of the invention will be set forth in the disclosure herein as well as the accompanying drawings. Such aspects may also be appreciated by those skilled in the art based on the disclosure herein.

To achieve these objects and other advantages and in accordance with the purpose of the invention, as embodied and broadly described herein, a mobile terminal according to one embodiment of the present invention may include a display, a band configured to be worn on a wrist of a user, a sensing unit configured to measure a blood flow rate in the wrist having the band worn thereon, and a controller controlling the display to display a running screen of a prescribed function if a variation of the measured blood flow rate is generated.

Preferably, the controller may determine a level of folding fingers of the user as one of a completely unfolded state, an intermediately folded state and a first made state based on the variation of the measured blood flow rate and the prescribed function may include a function mapped to the determined folded level.

More preferably, the controller may further determine whether an activity state of the user is a sleep state or an exercising state based on the measured blood flow rate and the prescribed function may correspond to the determined folded level and the determined activity state.

More preferably, in determining the activity state of the user, the controller may detect a heart rate of the user based on the measured blood flow rate. If the detected heart rate is equal to or greater than a prescribed numerical value, the controller may determine the activity state as the exercising state.

More preferably, in determining the activity state of the user, the controller may detect a heart rate of the user based on the measured blood flow rate. If the detected heart rate is smaller than a prescribed numerical value, the controller may determine the activity state as the sleep state.

More preferably, if the determined activity state of the user is the exercising state, the prescribed function may include an output function of an exercise summary information.

More preferably, the controller may output a notification to the user in response to an occurrence of a prescribed event. If the determined activity state of the user is the sleep state, the controller may control the notification not to be outputted despite the occurrence of the prescribed event.

In this case, the mobile terminal may further include a memory. The controller may save the non-outputted notification to be saved in the memory. And, the prescribed function may include a function of outputting the saved notification.

Preferably, if the variation of the measured blood flow rate is equal to or greater than a prescribed numerical value, the controller may display a running screen of the prescribed function.

Preferably, the mobile terminal may further include a wireless communication unit. And, the prescribed function may include a function of responding to a call signal received through the wireless communication unit.

In another aspect of the present invention, as embodied and broadly described herein, a method of controlling a mobile terminal wearable on a wrist of a user according to another embodiment of the present invention may include the steps of measuring a blood flow rate in the wrist having the mobile terminal worn thereon and controlling a display of the mobile terminal to display a running screen of a prescribed function if a variation of the measured blood flow rate is generated.

It is to be understood that both the foregoing general description and the following detailed description of the preferred embodiments of the present invention are exemplary and explanatory and are intended to provide further explanation of the invention as claimed.

BRIEF DESCRIPTION OF THE DRAWINGS

The present invention will become more fully understood from the detailed description given herein below and the accompanying drawings, which are given by illustration only, and thus are not limitative of the present invention, and wherein:

FIG. 1A is a block diagram of a mobile terminal in accordance with the present disclosure;

FIG. 4 is a diagram for a blood flow rate graph of a wrist varying in proportion to a folded level of fingers according to one embodiment of the present invention;

FIGS. 5A, 5B and 5C are diagrams for a control method of determining that a user is in a sleep state based on a heart rate and then running a function based on a result of the determination according to one embodiment of the present invention;

FIGS. 6A, 6B, 6C, 7A, 7B and 7C are diagrams for a control method of determining that a user is in a sleep state based on a heart rate and then running a function based on a result of the determination according to one embodiment of the present invention;

FIGS. 8A, 8B and 8C are diagrams for a control method of activating a display unit or running a prescribed function by detecting a finger folded level according to one embodiment of the present invention;

FIGS. 9A, 9B and 9C are diagrams for a control method of controlling an alarm based on a finger folded level in the course of outputting the alarm according to one embodiment of the present invention;

FIGS. 10A, 10B, and 10C are diagrams for a control method of controlling a video recording state according to one embodiment of the present invention;

FIGS. 11A, 11B and 11C are diagrams for a control method of detecting a finger folded level and then responding to a call signal using a result of the detection according to one embodiment of the present invention;

FIGS. 12A, 12B and 12C are diagrams for a control method of controlling a start/end of a recording in the course of a call based on a finger folded level according to one embodiment of the present invention;

FIGS. 13A, 13B and 13C are diagrams for a control method of controlling a call volume based on a folded level in the course of a call according to one embodiment of the present invention;

FIGS. 16A, 16B and 16C are diagrams for a control method of detecting a finger folded level and an input of rotating a wrist and then reading a received text based on a result of the detection according to one embodiment of the present invention;

FIGS. 19A, 19B and 19C are diagrams for a control method of taking a photo through an activated camera by detecting a finger folded level according to one embodiment of the present invention;

FIG. 22 is a diagram for a control method of unlocking a different mobile terminal 100 through an input of a knock with a hand having a watch type mobile terminal 300 worn thereon according to one embodiment of the present invention;

FIGS. 24A, 24B, 25A and 25B are diagrams for a control method of controlling a screen displayed through two layers according to one embodiment of the present invention.

DETAILED DESCRIPTION OF THE INVENTION

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

It will be understood that although the terms first, second, etc. may be used herein to describe various elements, these elements should not be limited by these terms. These terms are generally only used to distinguish one element from another.

It will be understood that when an element is referred to as being "connected with" another element, the element can be connected with the other element or intervening elements may also be present. In contrast, when an element is referred to as being "directly connected with" another element, there are no intervening elements present.

A singular representation may include a plural representation unless it represents a definitely different meaning from the context. Terms such as "include" or "has" are used herein and should be understood that they are intended to indicate an existence of several components, functions or steps, disclosed in the specification, and it is also understood that greater or fewer components, functions, or steps may likewise be utilized.

Mobile terminals presented herein may be implemented using a variety of different types of terminals. Examples of such terminals include cellular phones, smart phones, user equipment, laptop computers, digital broadcast terminals, personal digital assistants (PDAs), portable multimedia players (PMPs), navigators, portable computers (PCs), slate PCs, tablet PCs, ultra books, wearable devices (for example, smart watches, smart glasses, head mounted displays (HMDs)), and the like.

By way of non-limiting example only, further description will be made with reference to particular types of mobile terminals. However, such teachings apply equally to other types of terminals, such as those types noted above. In addition, these teachings may also be applied to stationary terminals such as digital TV, desktop computers, and the like.

Figure 1B:
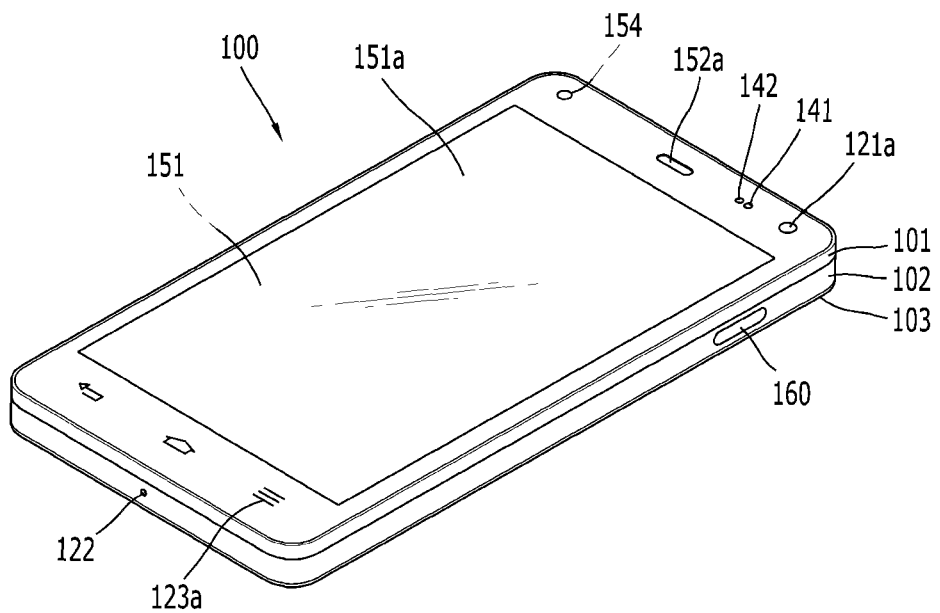
FIGS. 1B and 1C are conceptual views of one example of the mobile terminal, viewed from different directions.
Figure 1C:
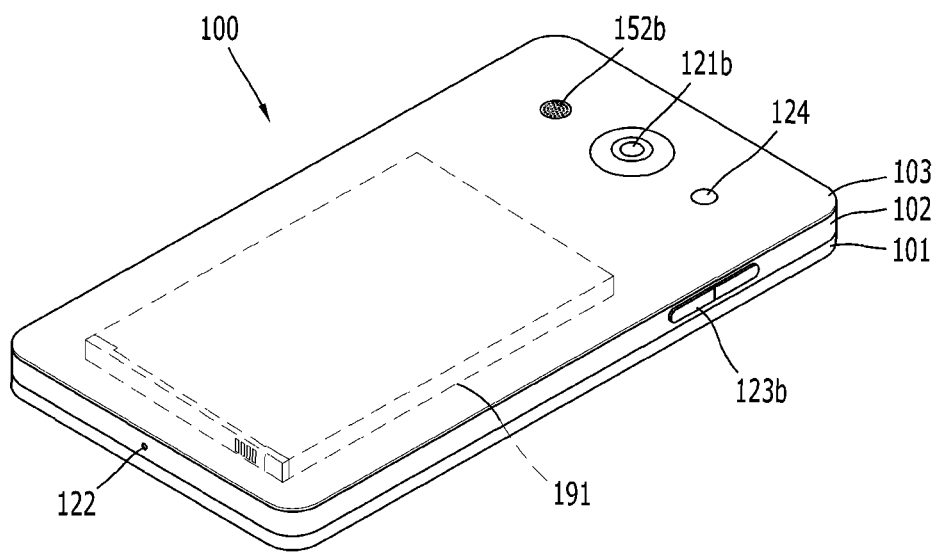

Reference is now made to FIGS. 1A-1C, where FIG. 1A is a block diagram of a mobile terminal in accordance with the present disclosure, and FIGS. 1B and 1C are conceptual views of one example of the mobile terminal, viewed from different directions.

The mobile terminal 100 is shown having components such as a wireless communication unit 110, an input unit 120, a sensing unit 140, an output unit 150, an interface unit 160, a memory 170, a controller 180, and a power supply unit 190. It is understood that implementing all of the illustrated components is not a requirement, and that greater or fewer components may alternatively be implemented.

Referring now to FIG. 1A, the mobile terminal 100 is shown having wireless communication unit 110 configured with several commonly implemented components. For instance, the wireless communication unit 110 typically includes one or more components which permit wireless communication between the mobile terminal 100 and a wireless communication system or network within which the mobile terminal is located.

The wireless communication unit 110 typically includes one or more modules which permit communications such as wireless communications between the mobile terminal 100 and a wireless communication system, communications between the mobile terminal 100 and another mobile terminal, communications between the mobile terminal 100 and an external server. Further, the wireless communication unit 110 typically includes one or more modules which connect the mobile terminal 100 to one or more networks. To facilitate such communications, the wireless communication unit 110 includes one or more of a broadcast receiving module 111, a mobile communication module 112, a wireless Internet module 113, a short-range communication module 114, and a location information module 115.

The input unit 120 includes a camera 121 for obtaining images or video, a microphone 122, which is one type of audio input device for inputting an audio signal, and a user input unit 123 (for example, a touch key, a push key, a mechanical key, a soft key, and the like) for allowing a user to input information. Data (for example, audio, video, image, and the like) is obtained by the input unit 120 and may be analyzed and processed by controller 180 according to device parameters, user commands, and combinations thereof.

The sensing unit 140 is typically implemented using one or more sensors configured to sense internal information of the mobile terminal, the surrounding environment of the mobile terminal, user information, and the like. For example, in FIG. 1A, the sensing unit 140 is shown having a proximity sensor 141 and an illumination sensor 142.

If desired, the sensing unit 140 may alternatively or additionally include other types of sensors or devices, such as a touch sensor, an acceleration sensor, a magnetic sensor, a G-sensor, a gyroscope sensor, a motion sensor, an RGB sensor, an infrared (IR) sensor, a finger scan sensor, a ultrasonic sensor, an optical sensor (for example, camera 121), a microphone 122, a battery gauge, an environment sensor (for example, a barometer, a hygrometer, a thermometer, a radiation detection sensor, a thermal sensor, and a gas sensor, among others), and a chemical sensor (for example, an electronic nose, a health care sensor, a biometric sensor, and the like), to name a few. The mobile terminal 100 may be configured to utilize information obtained from sensing unit 140, and in particular, information obtained from one or more sensors of the sensing unit 140, and combinations thereof.

The output unit 150 is typically configured to output various types of information, such as audio, video, tactile output, and the like. The output unit 150 is shown having a display unit 151, an audio output module 152, a haptic module 153, and an optical output module 154.

The display unit 151 may have an inter-layered structure or an integrated structure with a touch sensor in order to facilitate a touch screen. The touch screen may provide an output interface between the mobile terminal 100 and a user, as well as function as the user input unit 123 which provides an input interface between the mobile terminal 100 and the user.

The interface unit 160 serves as an interface with various types of external devices that can be coupled to the mobile terminal 100. The interface unit 160, for example, may include any of wired or wireless ports, external power supply ports, wired or wireless data ports, memory card ports, ports for connecting a device having an identification module, audio input/output (I/O) ports, video I/O ports, earphone ports, and the like. In some cases, the mobile terminal 100 may perform assorted control functions associated with a connected external device, in response to the external device being connected to the interface unit 160.

The memory 170 is typically implemented to store data to support various functions or features of the mobile terminal 100. For instance, the memory 170 may be configured to store application programs executed in the mobile terminal 100, data or instructions for operations of the mobile terminal 100, and the like. Some of these application programs may be downloaded from an external server via wireless communication. Other application programs may be installed within the mobile terminal 100 at time of manufacturing or shipping, which is typically the case for basic functions of the mobile terminal 100 (for example, receiving a call, placing a call, receiving a message, sending a message, and the like). It is common for application programs to be stored in the memory 170, installed in the mobile terminal 100, and executed by the controller 180 to perform an operation (or function) for the mobile terminal 100.

The controller 180 typically functions to control overall operation of the mobile terminal 100, in addition to the operations associated with the application programs. The controller 180 may provide or process information or functions appropriate for a user by processing signals, data, information and the like, which are input or output by the various components depicted in FIG. 1A, or activating application programs stored in the memory 170. As one example, the controller 180 controls some or all of the components illustrated in FIGS. 1A-1C according to the execution of an application program that have been stored in the memory 170.

The power supply unit 190 can be configured to receive external power or provide internal power in order to supply appropriate power required for operating elements and components included in the mobile terminal 100. The power supply unit 190 may include a battery, and the battery may be configured to be embedded in the terminal body, or configured to be detachable from the terminal body.

Referring still to FIG. 1A, various components depicted in this figure will now be described in more detail. Regarding the wireless communication unit 110, the broadcast receiving module 111 is typically configured to receive a broadcast signal and/or broadcast associated information from an external broadcast managing entity via a broadcast channel. The broadcast channel may include a satellite channel, a terrestrial channel, or both. In some embodiments, two or more broadcast receiving modules 111 may be utilized to facilitate simultaneously receiving of two or more broadcast channels, or to support switching among broadcast channels.

The mobile communication module 112 can transmit and/or receive wireless signals to and from one or more network entities. Typical examples of a network entity include a base station, an external mobile terminal, a server, and the like. Such network entities form part of a mobile communication network, which is constructed according to technical standards or communication methods for mobile communications (for example, Global System for Mobile Communication (GSM), Code Division Multi Access (CDMA), CDMA2000 (Code Division Multi Access 2000), EV-DO (Enhanced Voice-Data Optimized or Enhanced Voice-Data Only), Wideband CDMA (WCDMA), High Speed Downlink Packet access (HSDPA), HSUPA (High Speed Uplink Packet Access), Long Term Evolution (LTE), LTE-A (Long Term Evolution-Advanced), and the like). Examples of wireless signals transmitted and/or received via the mobile communication module 112 include audio call signals, video (telephony) call signals, or various formats of data to support communication of text and multimedia messages.

The wireless Internet module 113 is configured to facilitate wireless Internet access. This module may be internally or externally coupled to the mobile terminal 100. The wireless Internet module 113 may transmit and/or receive wireless signals via communication networks according to wireless Internet technologies.

Examples of such wireless Internet access include Wireless LAN (WLAN), Wireless Fidelity (Wi-Fi), Wi-Fi Direct, Digital Living Network Alliance (DLNA), Wireless Broadband (WiBro), Worldwide Interoperability for Microwave Access (WiMAX), High Speed Downlink Packet Access (HSDPA), HSUPA (High Speed Uplink Packet Access), Long Term Evolution (LTE), LTE-A (Long Term Evolution-Advanced), and the like. The wireless Internet module 113 may transmit/receive data according to one or more of such wireless Internet technologies, and other Internet technologies as well.

In some embodiments, when the wireless Internet access is implemented according to, for example, WiBro, HSDPA, HSUPA, GSM, CDMA, WCDMA, LTE, LTE-A and the like, as part of a mobile communication network, the wireless Internet module 113 performs such wireless Internet access. As such, the Internet module 113 may cooperate with, or function as, the mobile communication module 112.

The short-range communication module 114 is configured to facilitate short-range communications. Suitable technologies for implementing such short-range communications include BLUETOOTH™, Radio Frequency IDentification (RFID), Infrared Data Association (IrDA), Ultra-WideBand (UWB), ZigBee, Near Field Communication (NFC), Wireless-Fidelity (Wi-Fi), Wi-Fi Direct, Wireless USB (Wireless Universal Serial Bus), and the like. The short-range communication module 114 in general supports wireless communications between the mobile terminal 100 and a wireless communication system, communications between the mobile terminal 100 and another mobile terminal 100, or communications between the mobile terminal and a network where another mobile terminal 100 (or an external server) is located, via wireless area networks. One example of the wireless area networks is a wireless personal area networks.

In some embodiments, another mobile terminal (which may be configured similarly to mobile terminal 100) may be a wearable device, for example, a smart watch, a smart glass or a head mounted display (HMD), which is able to exchange data with the mobile terminal 100 (or otherwise cooperate with the mobile terminal 100). The short-range communication module 114 may sense or recognize the wearable device, and permit communication between the wearable device and the mobile terminal 100. In addition, when the sensed wearable device is a device which is authenticated to communicate with the mobile terminal 100, the controller 180, for example, may cause transmission of data processed in the mobile terminal 100 to the wearable device via the short-range communication module 114. Hence, a user of the wearable device may use the data processed in the mobile terminal 100 on the wearable device. For example, when a call is received in the mobile terminal 100, the user may answer the call using the wearable device. Also, when a message is received in the mobile terminal 100, the user can check the received message using the wearable device.

The location information module 115 is generally configured to detect, calculate, derive or otherwise identify a position of the mobile terminal. As an example, the location information module 115 includes a Global Position System (GPS) module, a Wi-Fi module, or both. If desired, the location information module 115 may alternatively or additionally function with any of the other modules of the wireless communication unit 110 to obtain data related to the position of the mobile terminal.

As one example, when the mobile terminal uses a GPS module, a position of the mobile terminal may be acquired using a signal sent from a GPS satellite. As another example, when the mobile terminal uses the Wi-Fi module, a position of the mobile terminal can be acquired based on information related to a wireless access point (AP) which transmits or receives a wireless signal to or from the Wi-Fi module.

The input unit 120 may be configured to permit various types of input to the mobile terminal 120. Examples of such input include audio, image, video, data, and user input. Image and video input is often obtained using one or more cameras 121. Such cameras 121 may process image frames of still pictures or video obtained by image sensors in a video or image capture mode. The processed image frames can be displayed on the display unit 151 or stored in memory 170. In some cases, the cameras 121 may be arranged in a matrix configuration to permit a plurality of images having various angles or focal points to be input to the mobile terminal 100. As another example, the cameras 121 may be located in a stereoscopic arrangement to acquire left and right images for implementing a stereoscopic image.

The microphone 122 is generally implemented to permit audio input to the mobile terminal 100. The audio input can be processed in various manners according to a function being executed in the mobile terminal 100. If desired, the microphone 122 may include assorted noise removing algorithms to remove unwanted noise generated in the course of receiving the external audio.

The user input unit 123 is a component that permits input by a user. Such user input may enable the controller 180 to control operation of the mobile terminal 100. The user input unit 123 may include one or more of a mechanical input element (for example, a key, a button located on a front and/or rear surface or a side surface of the mobile terminal 100, a dome switch, a jog wheel, a jog switch, and the like), or a touch-sensitive input, among others. As one example, the touch-sensitive input may be a virtual key or a soft key, which is displayed on a touch screen through software processing, or a touch key which is located on the mobile terminal at a location that is other than the touch screen. On the other hand, the virtual key or the visual key may be displayed on the touch screen in various shapes, for example, graphic, text, icon, video, or a combination thereof.

The sensing unit 140 is generally configured to sense one or more of internal information of the mobile terminal, surrounding environment information of the mobile terminal, user information, or the like. The controller 180 generally cooperates with the sending unit 140 to control operation of the mobile terminal 100 or execute data processing, a function or an operation associated with an application program installed in the mobile terminal based on the sensing provided by the sensing unit 140. The sensing unit 140 may be implemented using any of a variety of sensors, some of which will now be described in more detail.

The proximity sensor 141 may include a sensor to sense presence or absence of an object approaching a surface, or an object located near a surface, by using an electromagnetic field, infrared rays, or the like without a mechanical contact. The proximity sensor 141 may be arranged at an inner region of the mobile terminal covered by the touch screen, or near the touch screen.

The proximity sensor 141, for example, may include any of a transmissive type photoelectric sensor, a direct reflective type photoelectric sensor, a mirror reflective type photoelectric sensor, a high-frequency oscillation proximity sensor, a capacitance type proximity sensor, a magnetic type proximity sensor, an infrared rays proximity sensor, and the like. When the touch screen is implemented as a capacitance type, the proximity sensor 141 can sense proximity of a pointer relative to the touch screen by changes of an electromagnetic field, which is responsive to an approach of an object with conductivity. In this case, the touch screen (touch sensor) may also be categorized as a proximity sensor.

The term "proximity touch" will often be referred to herein to denote the scenario in which a pointer is positioned to be proximate to the touch screen without contacting the touch screen. The term "contact touch" will often be referred to herein to denote the scenario in which a pointer makes physical contact with the touch screen. For the position corresponding to the proximity touch of the pointer relative to the touch screen, such position will correspond to a position where the pointer is perpendicular to the touch screen. The proximity sensor 141 may sense proximity touch, and proximity touch patterns (for example, distance, direction, speed, time, position, moving status, and the like).

In general, controller 180 processes data corresponding to proximity touches and proximity touch patterns sensed by the proximity sensor 141, and cause output of visual information on the touch screen. In addition, the controller 180 can control the mobile terminal 100 to execute different operations or process different data according to whether a touch with respect to a point on the touch screen is either a proximity touch or a contact touch.

A touch sensor can sense a touch applied to the touch screen, such as display unit 151, using any of a variety of touch methods. Examples of such touch methods include a resistive type, a capacitive type, an infrared type, and a magnetic field type, among others.

As one example, the touch sensor may be configured to convert changes of pressure applied to a specific part of the display unit 151, or convert capacitance occurring at a specific part of the display unit 151, into electric input signals. The touch sensor may also be configured to sense not only a touched position and a touched area, but also touch pressure and/or touch capacitance. A touch object is generally used to apply a touch input to the touch sensor. Examples of typical touch objects include a finger, a touch pen, a stylus pen, a pointer, or the like.

When a touch input is sensed by a touch sensor, corresponding signals may be transmitted to a touch controller. The touch controller may process the received signals, and then transmit corresponding data to the controller 180. Accordingly, the controller 180 may sense which region of the display unit 151 has been touched. Here, the touch controller may be a component separate from the controller 180, the controller 180, and combinations thereof.

In some embodiments, the controller 180 may execute the same or different controls according to a type of touch object that touches the touch screen or a touch key provided in addition to the touch screen. Whether to execute the same or different control according to the object which provides a touch input may be decided based on a current operating state of the mobile terminal 100 or a currently executed application program, for example.

The touch sensor and the proximity sensor may be implemented individually, or in combination, to sense various types of touches. Such touches includes a short (or tap) touch, a long touch, a multi-touch, a drag touch, a flick touch, a pinch-in touch, a pinch-out touch, a swipe touch, a hovering touch, and the like.

If desired, an ultrasonic sensor may be implemented to recognize position information relating to a touch object using ultrasonic waves. The controller 180, for example, may calculate a position of a wave generation source based on information sensed by an illumination sensor and a plurality of ultrasonic sensors. Since light is much faster than ultrasonic waves, the time for which the light reaches the optical sensor is much shorter than the time for which the ultrasonic wave reaches the ultrasonic sensor. The position of the wave generation source may be calculated using this fact. For instance, the position of the wave generation source may be calculated using the time difference from the time that the ultrasonic wave reaches the sensor based on the light as a reference signal.

The camera 121 typically includes at least one a camera sensor (CCD, CMOS etc.), a photo sensor (or image sensors), and a laser sensor.

Implementing the camera 121 with a laser sensor may allow detection of a touch of a physical object with respect to a 3D stereoscopic image. The photo sensor may be laminated on, or overlapped with, the display device. The photo sensor may be configured to scan movement of the physical object in proximity to the touch screen. In more detail, the photo sensor may include photo diodes and transistors at rows and columns to scan content received at the photo sensor using an electrical signal which changes according to the quantity of applied light. Namely, the photo sensor may calculate the coordinates of the physical object according to variation of light to thus obtain position information of the physical object.

The display unit 151 is generally configured to output information processed in the mobile terminal 100. For example, the display unit 151 may display execution screen information of an application program executing at the mobile terminal 100 or user interface (UI) and graphic user interface (GUI) information in response to the execution screen information.

In some embodiments, the display unit 151 may be implemented as a stereoscopic display unit for displaying stereoscopic images. A typical stereoscopic display unit may employ a stereoscopic display scheme such as a stereoscopic scheme (a glass scheme), an auto-stereoscopic scheme (glassless scheme), a projection scheme (holographic scheme), or the like.

The audio output module 152 is generally configured to output audio data. Such audio data may be obtained from any of a number of different sources, such that the audio data may be received from the wireless communication unit 110 or may have been stored in the memory 170. The audio data may be output during modes such as a signal reception mode, a call mode, a record mode, a voice recognition mode, a broadcast reception mode, and the like. The audio output module 152 can provide audible output related to a particular function (e.g., a call signal reception sound, a message reception sound, etc.) performed by the mobile terminal 100. The audio output module 152 may also be implemented as a receiver, a speaker, a buzzer, or the like.

A haptic module 153 can be configured to generate various tactile effects that a user feels, perceive, or otherwise experience. A typical example of a tactile effect generated by the haptic module 153 is vibration. The strength, pattern and the like of the vibration generated by the haptic module 153 can be controlled by user selection or setting by the controller. For example, the haptic module 153 may output different vibrations in a combining manner or a sequential manner.

Besides vibration, the haptic module 153 can generate various other tactile effects, including an effect by stimulation such as a pin arrangement vertically moving to contact skin, a spray force or suction force of air through a jet orifice or a suction opening, a touch to the skin, a contact of an electrode, electrostatic force, an effect by reproducing the sense of cold and warmth using an element that can absorb or generate heat, and the like.

The haptic module 153 can also be implemented to allow the user to feel a tactile effect through a muscle sensation such as the user's fingers or arm, as well as transferring the tactile effect through direct contact. Two or more haptic modules 153 may be provided according to the particular configuration of the mobile terminal 100.

An optical output module 154 can output a signal for indicating an event generation using light of a light source. Examples of events generated in the mobile terminal 100 may include message reception, call signal reception, a missed call, an alarm, a schedule notice, an email reception, information reception through an application, and the like.

A signal output by the optical output module 154 may be implemented in such a manner that the mobile terminal emits monochromatic light or light with a plurality of colors. The signal output may be terminated as the mobile terminal senses that a user has checked the generated event, for example.

The interface unit 160 serves as an interface for external devices to be connected with the mobile terminal 100. For example, the interface unit 160 can receive data transmitted from an external device, receive power to transfer to elements and components within the mobile terminal 100, or transmit internal data of the mobile terminal 100 to such external device. The interface unit 160 may include wired or wireless headset ports, external power supply ports, wired or wireless data ports, memory card ports, ports for connecting a device having an identification module, audio input/output (I/O) ports, video I/O ports, earphone ports, or the like.

The identification module may be a chip that stores various information for authenticating authority of using the mobile terminal 100 and may include a user identity module (UIM), a subscriber identity module (SIM), a universal subscriber identity module (USIM), and the like. In addition, the device having the identification module (also referred to herein as an "identifying device") may take the form of a smart card. Accordingly, the identifying device can be connected with the terminal 100 via the interface unit 160.

When the mobile terminal 100 is connected with an external cradle, the interface unit 160 can serve as a passage to allow power from the cradle to be supplied to the mobile terminal 100 or may serve as a passage to allow various command signals input by the user from the cradle to be transferred to the mobile terminal there through. Various command signals or power input from the cradle may operate as signals for recognizing that the mobile terminal is properly mounted on the cradle.

The memory 170 can store programs to support operations of the controller 180 and store input/output data (for example, phonebook, messages, still images, videos, etc.). The memory 170 may store data related to various patterns of vibrations and audio which are output in response to touch inputs on the touch screen.

The memory 170 may include one or more types of storage mediums including a Flash memory, a hard disk, a solid state disk, a silicon disk, a multimedia card micro type, a card-type memory (e.g., SD or DX memory, etc), a Random Access Memory (RAM), a Static Random Access Memory (SRAM), a Read-Only Memory (ROM), an Electrically Erasable Programmable Read-Only Memory (EEPROM), a Programmable Read-Only memory (PROM), a magnetic memory, a magnetic disk, an optical disk, and the like. The mobile terminal 100 may also be operated in relation to a network storage device that performs the storage function of the memory 170 over a network, such as the Internet.

The controller 180 may typically control the general operations of the mobile terminal 100. For example, the controller 180 may set or release a lock state for restricting a user from inputting a control command with respect to applications when a status of the mobile terminal meets a preset condition.

The controller 180 can also perform the controlling and processing associated with voice calls, data communications, video calls, and the like, or perform pattern recognition processing to recognize a handwriting input or a picture drawing input performed on the touch screen as characters or images, respectively. In addition, the controller 180 can control one or a combination of those components in order to implement various exemplary embodiments disclosed herein.

The power supply unit 190 receives external power or provide internal power and supply the appropriate power required for operating respective elements and components included in the mobile terminal 100. The power supply unit 190 may include a battery, which is typically rechargeable or be detachably coupled to the terminal body for charging.

The power supply unit 190 may include a connection port. The connection port may be configured as one example of the interface unit 160 to which an external charger for supplying power to recharge the battery is electrically connected.

As another example, the power supply unit 190 may be configured to recharge the battery in a wireless manner without use of the connection port. In this example, the power supply unit 190 can receive power, transferred from an external wireless power transmitter, using at least one of an inductive coupling method which is based on magnetic induction or a magnetic resonance coupling method which is based on electromagnetic resonance.

Various embodiments described herein may be implemented in a computer-readable medium, a machine-readable medium, or similar medium using, for example, software, hardware, or any combination thereof.

Referring now to FIGS. 1B and 1C, the mobile terminal 100 is described with reference to a bar-type terminal body. However, the mobile terminal 100 may alternatively be implemented in any of a variety of different configurations. Examples of such configurations include watch-type, clip-type, glasses-type, or as a folder-type, flip-type, slide-type, swing-type, and swivel-type in which two and more bodies are combined with each other in a relatively movable manner, and combinations thereof. Discussion herein will often relate to a particular type of mobile terminal (for example, bar-type, watch-type, glasses-type, and the like). However, such teachings with regard to a particular type of mobile terminal will generally apply to other types of mobile terminals as well.

The mobile terminal 100 will generally include a case (for example, frame, housing, cover, and the like) forming the appearance of the terminal. In this embodiment, the case is formed using a front case 101 and a rear case 102. Various electronic components are incorporated into a space formed between the front case 101 and the rear case 102. At least one middle case may be additionally positioned between the front case 101 and the rear case 102.

The display unit 151 is shown located on the front side of the terminal body to output information. As illustrated, a window 151a of the display unit 151 may be mounted to the front case 101 to form the front surface of the terminal body together with the front case 101.

In some embodiments, electronic components may also be mounted to the rear case 102. Examples of such electronic components include a detachable battery 191, an identification module, a memory card, and the like. Rear cover 103 is shown covering the electronic components, and this cover may be detachably coupled to the rear case 102. Therefore, when the rear cover 103 is detached from the rear case 102, the electronic components mounted to the rear case 102 are externally exposed.

As illustrated, when the rear cover 103 is coupled to the rear case 102, a side surface of the rear case 102 is partially exposed. In some cases, upon the coupling, the rear case 102 may also be completely shielded by the rear cover 103. In some embodiments, the rear cover 103 may include an opening for externally exposing a camera 121b or an audio output module 152b.

The cases 101, 102, 103 may be formed by injection-molding synthetic resin or may be formed of a metal, for example, stainless steel (STS), aluminum (Al), titanium (Ti), or the like.

As an alternative to the example in which the plurality of cases form an inner space for accommodating components, the mobile terminal 100 may be configured such that one case forms the inner space. In this example, a mobile terminal 100 having a uni-body is formed in such a manner that synthetic resin or metal extends from a side surface to a rear surface.

If desired, the mobile terminal 100 may include a waterproofing unit (not shown) for preventing introduction of water into the terminal body. For example, the waterproofing unit may include a waterproofing member which is located between the window 151a and the front case 101, between the front case 101 and the rear case 102, or between the rear case 102 and the rear cover 103, to hermetically seal an inner space when those cases are coupled.

FIGS. 1B and 1C depict certain components as arranged on the mobile terminal. However, it is to be understood that alternative arrangements are possible and within the teachings of the instant disclosure. Some components may be omitted or rearranged. For example, the first manipulation unit 123a may be located on another surface of the terminal body, and the second audio output module 152b may be located on the side surface of the terminal body.

The display unit 151 outputs information processed in the mobile terminal 100. The display unit 151 may be implemented using one or more suitable display devices. Examples of such suitable display devices include a liquid crystal display (LCD), a thin film transistor-liquid crystal display (TFT-LCD), an organic light emitting diode (OLED), a flexible display, a 3-dimensional (3D) display, an e-ink display, and combinations thereof.

The display unit 151 may be implemented using two display devices, which can implement the same or different display technology. For instance, a plurality of the display units 151 may be arranged on one side, either spaced apart from each other, or these devices may be integrated, or these devices may be arranged on different surfaces.

The display unit 151 may also include a touch sensor which senses a touch input received at the display unit. When a touch is input to the display unit 151, the touch sensor may be configured to sense this touch and the controller 180, for example, may generate a control command or other signal corresponding to the touch. The content which is input in the touching manner may be a text or numerical value, or a menu item which can be indicated or designated in various modes.

The touch sensor may be configured in a form of a film having a touch pattern, disposed between the window 151a and a display on a rear surface of the window 151a, or a metal wire which is patterned directly on the rear surface of the window 151a. Alternatively, the touch sensor may be integrally formed with the display. For example, the touch sensor may be disposed on a substrate of the display or within the display.

The display unit 151 may also form a touch screen together with the touch sensor. Here, the touch screen may serve as the user input unit 123 (see FIG. 1A). Therefore, the touch screen may replace at least some of the functions of the first manipulation unit 123a.

The first audio output module 152a may be implemented in the form of a speaker to output voice audio, alarm sounds, multimedia audio reproduction, and the like.

The window 151a of the display unit 151 will typically include an aperture to permit audio generated by the first audio output module 152a to pass. One alternative is to allow audio to be released along an assembly gap between the structural bodies (for example, a gap between the window 151a and the front case 101). In this case, a hole independently formed to output audio sounds may not be seen or is otherwise hidden in terms of appearance, thereby further simplifying the appearance and manufacturing of the mobile terminal 100.

The optical output module 154 can be configured to output light for indicating an event generation. Examples of such events include a message reception, a call signal reception, a missed call, an alarm, a schedule notice, an email reception, information reception through an application, and the like. When a user has checked a generated event, the controller can control the optical output unit 154 to stop the light output.

The first camera 121a can process image frames such as still or moving images obtained by the image sensor in a capture mode or a video call mode. The processed image frames can then be displayed on the display unit 151 or stored in the memory 170.

The first and second manipulation units 123a and 123b are examples of the user input unit 123, which may be manipulated by a user to provide input to the mobile terminal 100. The first and second manipulation units 123a and 123b may also be commonly referred to as a manipulating portion, and may employ any tactile method that allows the user to perform manipulation such as touch, push, scroll, or the like. The first and second manipulation units 123a and 123b may also employ any non-tactile method that allows the user to perform manipulation such as proximity touch, hovering, or the like.

FIG. 1B illustrates the first manipulation unit 123a as a touch key, but possible alternatives include a mechanical key, a push key, a touch key, and combinations thereof.

Input received at the first and second manipulation units 123a and 123b may be used in various ways. For example, the first manipulation unit 123a may be used by the user to provide an input to a menu, home key, cancel, search, or the like, and the second manipulation unit 123b may be used by the user to provide an input to control a volume level being output from the first or second audio output modules 152a or 152b, to switch to a touch recognition mode of the display unit 151, or the like.

As another example of the user input unit 123, a rear input unit (not shown) may be located on the rear surface of the terminal body. The rear input unit can be manipulated by a user to provide input to the mobile terminal 100. The input may be used in a variety of different ways. For example, the rear input unit may be used by the user to provide an input for power on/off, start, end, scroll, control volume level being output from the first or second audio output modules 152a or 152b, switch to a touch recognition mode of the display unit 151, and the like. The rear input unit may be configured to permit touch input, a push input, or combinations thereof.

The rear input unit may be located to overlap the display unit 151 of the front side in a thickness direction of the terminal body. As one example, the rear input unit may be located on an upper end portion of the rear side of the terminal body such that a user can easily manipulate it using a forefinger when the user grabs the terminal body with one hand. Alternatively, the rear input unit can be positioned at most any location of the rear side of the terminal body.

Embodiments that include the rear input unit may implement some or all of the functionality of the first manipulation unit 123a in the rear input unit. As such, in situations where the first manipulation unit 123a is omitted from the front side, the display unit 151 can have a larger screen.

As a further alternative, the mobile terminal 100 may include a finger scan sensor which scans a user's fingerprint. The controller 180 can then use fingerprint information sensed by the finger scan sensor as part of an authentication procedure. The finger scan sensor may also be installed in the display unit 151 or implemented in the user input unit 123.

The microphone 122 is shown located at an end of the mobile terminal 100, but other locations are possible. If desired, multiple microphones may be implemented, with such an arrangement permitting the receiving of stereo sounds.

The interface unit 160 may serve as a path allowing the mobile terminal 100 to interface with external devices. For example, the interface unit 160 may include one or more of a connection terminal for connecting to another device (for example, an earphone, an external speaker, or the like), a port for near field communication (for example, an Infrared Data Association (IrDA) port, a Bluetooth port, a wireless LAN port, and the like), or a power supply terminal for supplying power to the mobile terminal 100. The interface unit 160 may be implemented in the form of a socket for accommodating an external card, such as Subscriber Identification Module (SIM), User Identity Module (UIM), or a memory card for information storage.

The second camera 121b is shown located at the rear side of the terminal body and includes an image capturing direction that is substantially opposite to the image capturing direction of the first camera unit 121a. If desired, second camera 121a may alternatively be located at other locations, or made to be moveable, in order to have a different image capturing direction from that which is shown.

The second camera 121b can include a plurality of lenses arranged along at least one line. The plurality of lenses may also be arranged in a matrix configuration. The cameras may be referred to as an "array camera." When the second camera 121b is implemented as an array camera, images may be captured in various manners using the plurality of lenses and images with better qualities.

As shown in FIG. 1C, a flash 124 is shown adjacent to the second camera 121b. When an image of a subject is captured with the camera 121b, the flash 124 may illuminate the subject.

As shown in FIG. 1B, the second audio output module 152b can be located on the terminal body. The second audio output module 152b may implement stereophonic sound functions in conjunction with the first audio output module 152a, and may be also used for implementing a speaker phone mode for call communication.

At least one antenna for wireless communication may be located on the terminal body. The antenna may be installed in the terminal body or formed by the case. For example, an antenna which configures a part of the broadcast receiving module 111 may be retractable into the terminal body. Alternatively, an antenna may be formed using a film attached to an inner surface of the rear cover 103, or a case that includes a conductive material.

A power supply unit 190 for supplying power to the mobile terminal 100 may include a battery 191, which is mounted in the terminal body or detachably coupled to an outside of the terminal body. The battery 191 may receive power via a power source cable connected to the interface unit 160. Also, the battery 191 can be recharged in a wireless manner using a wireless charger. Wireless charging may be implemented by magnetic induction or electromagnetic resonance.

The rear cover 103 is shown coupled to the rear case 102 for shielding the battery 191, to prevent separation of the battery 191, and to protect the battery 191 from an external impact or from foreign material. When the battery 191 is detachable from the terminal body, the rear case 103 may be detachably coupled to the rear case 102.

An accessory for protecting an appearance or assisting or extending the functions of the mobile terminal 100 can also be provided on the mobile terminal 100. As one example of an accessory, a cover or pouch for covering or accommodating at least one surface of the mobile terminal 100 may be provided. The cover or pouch may cooperate with the display unit 151 to extend the function of the mobile terminal 100. Another example of the accessory is a touch pen for assisting or extending a touch input to a touch screen.

In accordance with still further embodiments, a mobile terminal may be configured as a device which is wearable on a human body. Such devices go beyond the usual technique of a user grasping the mobile terminal using their hand. Examples of the wearable device include a smart watch, a smart glass, a head mounted display (HMD), and the like.

A typical wearable device can exchange data with (or cooperate with) another mobile terminal 100. In such a device, the wearable device generally has functionality that is less than the cooperating mobile terminal. For instance, the short-range communication module 114 of a mobile terminal 100 may sense or recognize a wearable device that is near-enough to communicate with the mobile terminal. In addition, when the sensed wearable device is a device which is authenticated to communicate with the mobile terminal 100, the controller 180 may transmit data processed in the mobile terminal 100 to the wearable device via the short-range communication module 114, for example. Hence, a user of the wearable device can use the data processed in the mobile terminal 100 on the wearable device. For example, when a call is received in the mobile terminal 100, the user can answer the call using the wearable device. Also, when a message is received in the mobile terminal 100, the user can check the received message using the wearable device.

Figure 2A:
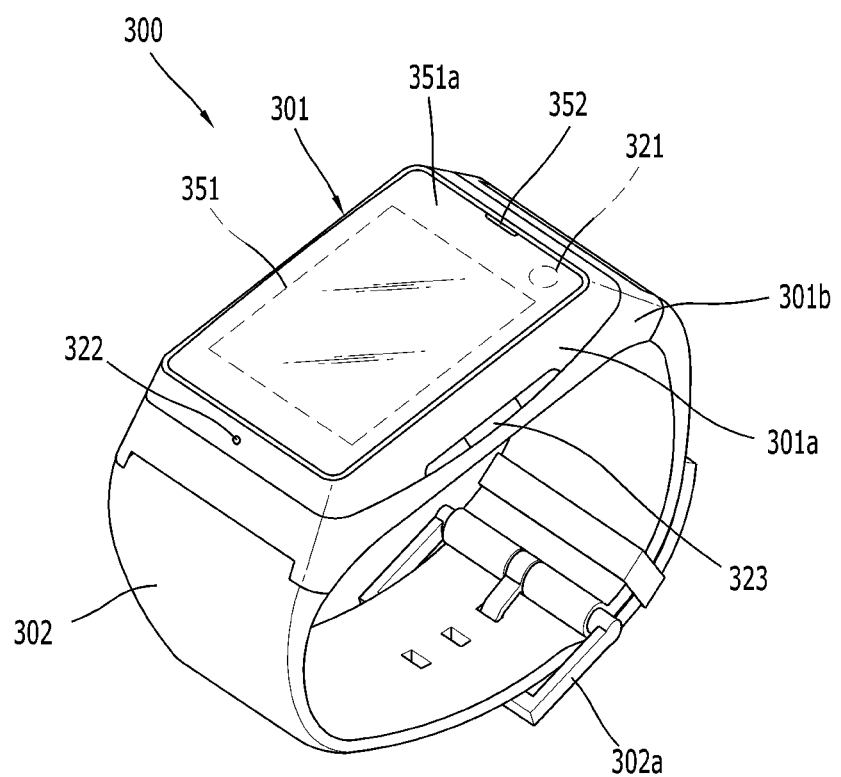
FIG. 2A is a perspective diagram for one example of a mobile terminal 300 of a watch type related to another embodiment of the present invention.

FIG. 2A is a perspective view illustrating one example of a watch-type mobile terminal 300 in accordance with another exemplary embodiment. As illustrated in FIG. 3, the watch-type mobile terminal 300 includes a main body 301 with a display unit 351 and a band 302 connected to the main body 301 to be wearable on a wrist. In general, mobile terminal 300 may be configured to include features that are the same or similar to that of mobile terminal 100 of FIGS. 1A-1C.

The main body 301 may include a case having a certain appearance. As illustrated, the case may include a first case 301a and a second case 301b cooperatively defining an inner space for accommodating various electronic components. Other configurations are possible. For instance, a single case may alternatively be implemented, with such a case being configured to define the inner space, thereby implementing a mobile terminal 300 with a uni-body.

The watch-type mobile terminal 300 can perform wireless communication, and an antenna for the wireless communication can be installed in the main body 301. The antenna may extend its function using the case. For example, a case including a conductive material may be electrically connected to the antenna to extend a ground area or a radiation area.

The display unit 351 is shown located at the front side of the main body 301 so that displayed information is viewable to a user. In some embodiments, the display unit 351 includes a touch sensor so that the display unit can function as a touch screen. As illustrated, window 351a is positioned on the first case 301a to form a front surface of the terminal body together with the first case 301a.

The illustrated embodiment includes audio output module 352, a camera 321, a microphone 322, and a user input unit 323 positioned on the main body 301. When the display unit 351 is implemented as a touch screen, additional function keys may be minimized or eliminated. For example, when the touch screen is implemented, the user input unit 323 may be omitted.

The band 302 is commonly worn on the user's wrist and may be made of a flexible material for facilitating wearing of the device. As one example, the band 302 may be made of fur, rubber, silicon, synthetic resin, or the like. The band 302 may also be configured to be detachable from the main body 301. Accordingly, the band 302 may be replaceable with various types of bands according to a user's preference.

In one configuration, the band 302 may be used for extending the performance of the antenna. For example, the band may include therein a ground extending portion (not shown) electrically connected to the antenna to extend a ground area.

The band 302 may include fastener 302a. The fastener 302a may be implemented into a buckle type, a snap-fit hook structure, a Velcro® type, or the like, and include a flexible section or material. The drawing illustrates an example that the fastener 302a is implemented using a buckle.

Further preferred embodiments will be described in more detail with reference to additional drawing figures. It is understood by those skilled in the art that the present features can be embodied in several forms without departing from the characteristics thereof.

In the following detailed description, reference is made to the accompanying drawing figures which form a part hereof, and which show by way of illustration specific embodiments of the invention. It is to be understood by those of ordinary skill in this technological field that other embodiments may be utilized, and structural, electrical, as well as procedural changes may be made without departing from the scope of the present invention. Wherever possible, the same reference numbers will be used throughout the drawings to refer to the same or similar parts.

Since the above-described mobile terminal 300 of the watch type has limitations put on its configuration, it is not easy to input a user command to the mobile terminal 300 of the watch type. Namely, although a display unit 351 of a touchscreen type is employed, a size of the display unit 351 is limited and a size of a body 301 is not enough to include a user input unit 123 of another type.

Therefore, according to one embodiment of the present invention, it is intended to provide a control method for controlling the mobile terminal 300 of the watch type in a manner of detecting a user's motion (e.g., a motion of a hand having the watch type mobile terminal 300 worn thereon, etc.) through sensors providable to the mobile terminal 300 of the watch type and then using the detected motion.

According to one embodiment of the present invention, a detected user's motion may include a state that fingers of a hand having the watch type mobile terminal 300 worn thereon are folded. In particular, after a motion such as a state that a user closes user's fist by folding fingers, a state that a user fully spreads out fingers, a state that a user fold fingers half, or the like has been detected, it is able to control a prescribed function to be run based on a result of the detection. Runnable functions shall be described in detail with reference to the accompanying drawings later.

According to one embodiment of the present invention, in order to determine the finger folded state, it is proposed to use a blood flow sensor.

In particular, the blood flow sensor is a device capable of measuring a relative density of a blood flowing in a specific part of an examinee body in a manner of applying infrared rays to the specific part of the examinee body and then measuring a reflected light quantity (or a transmitted light quantity). In case of applying infrared rays, if a density of blood is high, since more light is absorbed, a reflected or transmitted light quantity will be lowered. On the contrary, if a density of blood is low, a reflected or transmitted light quantity will be will be raised. Hence, in case of using the blood flow sensor, although it is difficult to measure an accurate blood pressure, it is possible to measure a variation of a blood flow rate of an examined part.

Meanwhile, a heartbeat generated from contraction and relaxation is delivered to a whole body along blood. If a density variation of a blood caused by the heartbeat is observed, it is able to detect the heartbeat. Hence, the blood flow sensor may be called a PPG (photoplethysmogram sensor).

Since a level of the current consumed by the blood flow sensor in an activated state is lower than those of other sensors, usability of the blood flow sensor is high. A consumed current amount of a currently mass-produced blood flow sensor in sleep mode is about 193.3 µA. And, a consumed current amount of a blood flow sensor produced in the future may be lowered to about 100 µA.

Figure 2B:
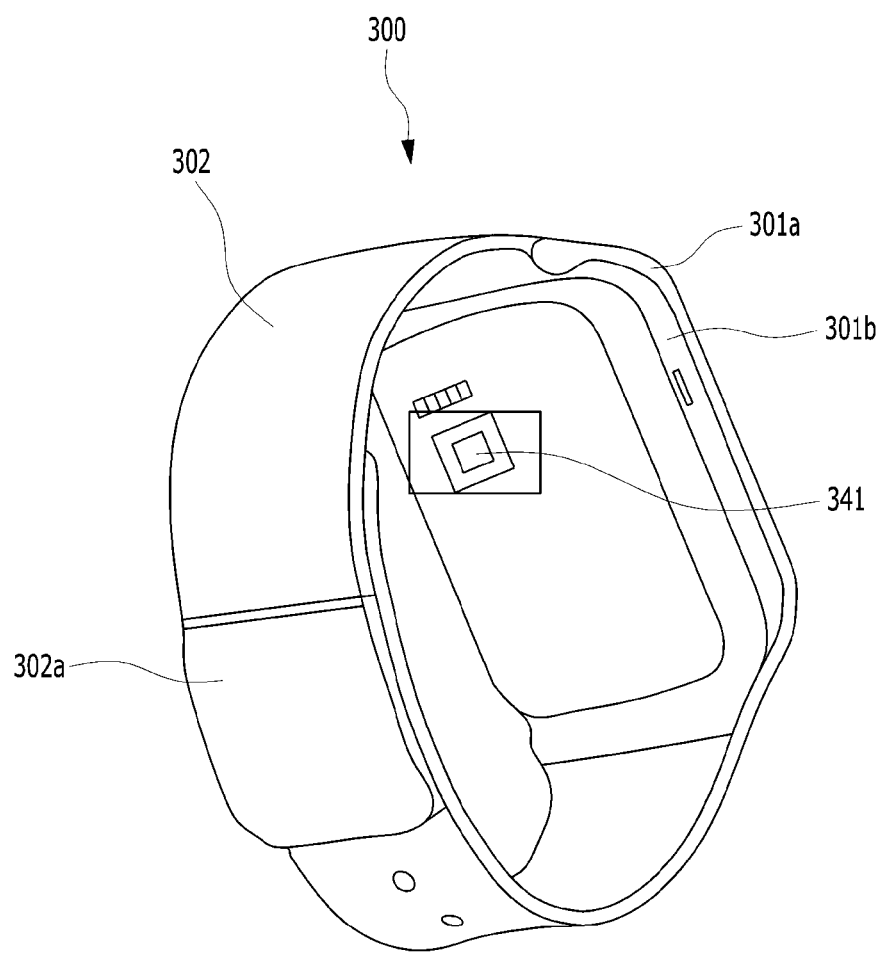
FIG. 2B is a rear perspective diagram for one example of a mobile terminal 300 of a watch type related to another embodiment of the present invention.

FIG. 2B is a rear perspective diagram for one example of a mobile terminal 300 of a watch type related to another embodiment of the present invention.

Referring to FIG. 2B, a blood flow sensor 341 can be provided onto a $2^{nd}$ case 301b, which comes into contact with a wrist of a user currently wearing the mobile terminal 300 of the watch type according to one embodiment of the present invention, of a body 310 of the mobile terminal 300 of the watch type. The location of the blood flow sensor 341 is exemplary only, by which the blood flow sensor 341 is non-limited.

While the user wears the mobile terminal 300 of the watch type, it is able to determine a blood flow rate of the user's wrist through the blood flow sensor 341. According to one embodiment of the present invention, it is proposed to determine a finger folded level based on the blood flow rate of the wrist. Such an embodiment is described in detail with reference to FIGS. 3A to 4 as follows.

Figure 3A:
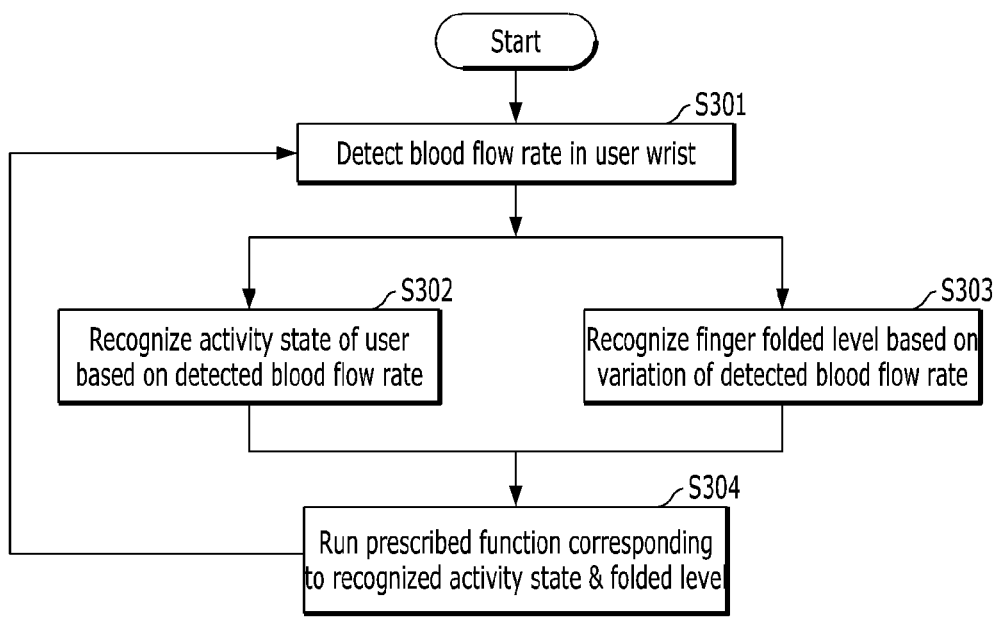
FIG. 3A and FIG. 3B are flowcharts for a control method of detecting a blood flow rate and then running a prescribed function based on the detected blood flow rate according to one embodiment of the present invention.
Figure 3B:
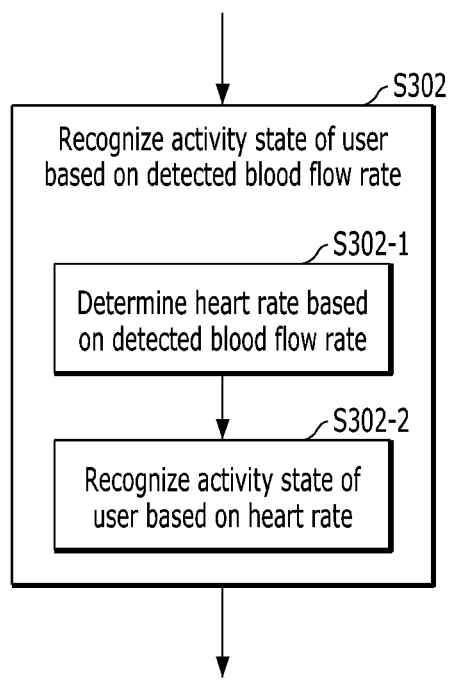

FIG. 3A and FIG. 3B are flowcharts for a control method of detecting a blood flow rate and then running a prescribed function based on the detected blood flow rate according to one embodiment of the present invention. And, FIG. 4 is a diagram for a blood flow rate graph of a wrist varying in proportion to a folded level of fingers according to one embodiment of the present invention. The following description is made with reference to FIGS. 3A to 4.

First of all, in a step S301, the mobile terminal 300 of the watch type detects a blood flow rate of a user wrist using a blood flow sensor. In a step S302, the mobile terminal 300 of the watch type is able to recognize a user's activity state based on the blood flow rate detected in the step S301. In this case, the user's activity state means a state that can vary a heart rate of the user like an exercising state, a sleep state, or the like. A detailed determining method is described with reference to FIG. 3B as follows.

FIG. 3B is a flowchart of detailed steps of the step S302. Referring to FIG. 3B, in a step S302-1, the controller 180 determines a heart rate based on the detected blood flow rate. In a step S302-2, the controller 180 can recognize a user's activity state based on the determined heart rate. Generally, a heart rate in the exercising state is higher than that in a normal state. Hence, if a heart rate per unit time is equal to or greater than a prescribed reference, the controller 180 may be able to recognize that the user is in the exercising state. Generally, a heart rate in the sleep state is lower than that in a normal state. Hence, if a heart rate per unit time is smaller than a prescribed reference, the controller 180 may be able to recognize that the user is in the sleep state. In particular, in the step S302-2, by checking a level of the heart rate, it may be able to recognize the exercising state of the user.

In a step S303, the mobile terminal 300 of the watch type is able to recognize a finger folded level based on the detected blood flow rate. A detailed method is described with reference to the graph shown in FIG. 4.

FIG. 4 is a graph of numerical values of a blood flow rate detected through the blood flow sensor 341 in accordance with a flow of time. Referring to the graph, the x-axis indicates a time axis, while the y-axis indicates a blood flow rate of a wrist.

In case that a user makes a fist by folding all fingers, a flow of blood delivered to a whole hand including the fingers is interrupted. As the flow of the blood delivered to the hand is interrupted, a density of the blood flowing in the wrist is increased. On the other hand, if all the fingers are spread out, the flow of blood becomes smooth so that the density of the blood flowing in the wrist can be decreased. Since the blood flow sensor determines a quantity of the flowing blood using the measured blood density, the measured blood flow rate may be varied in accordance with the density as well. Hence, in case that the blood flow sensor is located at the wrist of the user, as shown in FIG. 2B, it may be able to determine a user finger folded level using the measured blood flow rate value.

A $1^{st}$ interval of the graph shown in FIG. 4 indicates a waveform of an interval in which a user completely unfolds fingers. In this interval, since a flow of blood is smooth, numerical values of the measured blood flow rate may be included in a relatively low numerical value (i.e., a $1^{st}$ numerical value range). And, this numerical value of the blood flow rate may be lower than a numerical value of a normal blood flow rate. A $2^{nd}$ interval indicates a waveform of an interval in which a user makes a fist by completely folding fingers. In this interval, since a flow of blood is not smooth, numerical values of the measured blood flow rate may be included in a relatively high numerical value (i.e., a $2^{nd}$ numerical value range). And, this numerical value of the blood flow rate may be higher than a numerical value of a normal blood flow rate. A $3^{rd}$ interval indicates a waveform of an interval in which a user folds fingers about half and has a numerical value of a blood flow rate included in an intermediate numerical value (i.e., a $3^{rd}$ numerical value range) between the numerical value range of the Pt interval and the numerical value range of the $2^{nd}$ interval.

According to another embodiment of the present invention, it is able to determine an action of closing and opening a fist in accordance with a variation of a blood flow rate value. In particular, if a blood flow rate value varies in a manner of increasing over a prescribed numerical value, it is able to determine that a user opens and then closes a fist. Likewise, if a blood flow rate value varies in a manner of decreasing over a prescribed numerical value, it is able to determine that a user closes and then opens a fist. In particular, the mobile terminal 300 of the watch type may be able to determine a level of closing a user's fist in accordance with a variation of a measured blood flow rate value.

In particular, when the graph is analyzed, it may be able to determine a fist closed level (or a fist folded level) in accordance with a value of a measured blood flow rate and/or a variation of a blood flow rate. Moreover, since a value of a measured blood flow rate may vary for each user or each worn state, it may be able to determine a more accurate state in a manner of checking a value of a blood flow rate in accordance with a finger folded state of a user and then analyzing the measured value of the blood flow rate.

Meanwhile, if a waveform of a blood flow rate is enlarged irrespective of a level of the blood flow rate, it is able to observe waveforms 401-1 to 401-3 that vibrate in accordance with heartbeats.

According to one embodiment of the present invention mentioned in the following description, assume that a finger folded state of a user can be determined by the above-described method. Particularly, according to the aforementioned embodiment, a finger folded state can be classified into one of three states (i.e., a fully unfolded state, a fully folded state, and a half folded state). Furthermore, the finger folded state may be classified into more states depending on a finger folded level.

For clarity of the following description, an input (state) of completely unfolding (or spreading out) fingers shall be named a palm input (state), an input (state) of completely folding fingers shall be named a fist input (state), and an input (state) of half folding fingers shall be named a folding input (state).

Meanwhile, as mentioned in the foregoing description, it is able to detect a heartbeat using a result of detection through a blood flow sensor. According to one embodiment of the present invention, it is proposed to determine a current activity state of a user based on a detected heart rate and it is also proposed to run a function in consideration of both an activity state and a finger folded level.

In particular, in a step S304, the mobile terminal 300 of the watch type runs a prescribed function mapped to the recognized activity state and the folded level and is then able to return to the step S301. In this case, the run prescribed function may include one of the functions that will be run with reference to FIGS. 5A to 25B. Meanwhile, the functions run with reference to FIGS. 5A to 25B may be run individually. Moreover, it is possible for a plurality of the functions to be used in a manner of being combined together. In particular, in case that a plurality of the functions are used by being combined together, the functions may be run in a manner of being distinguished from each other through classification of gestures.

FIGS. 5A, 5B and 5C are diagrams for a control method of determining that a user is in a sleep state based on a heart rate and then running a function based on a result of the determination according to one embodiment of the present invention.

As mentioned in the foregoing description, a heart rate in a sleep state is lower than that in a normal state in general. Hence, if a heart rate per unit time is equal to or smaller than a prescribed reference, the controller 180 may be able to determine that a user is in a sleep state.

In FIG. 5A, the controller 180 is assumed as determining that a user is in a sleep state as a result from detecting a heart rate of the user using the aforementioned method. If it is determined that the user is in the sleep state, the controller 180 can control a generated notification not to be outputted to the user. The reason for this is that the output of the notification may interrupt the user's sleep. The notification failing to be outputted is saved in turn. When the user wakes up, the user can be informed of the saved notifications in a manner that the saved notifications are outputted [FIG. 5C].

According to one embodiment of the present invention, when a user awakes from a sleep state, it is proposed to output a weather information to the user [FIG. 5B]. The reason for this is that the weather is most useful information in the morning. After detecting that the user has got out of the sleep state, if a prescribed user command is received, the controller 180 can output the weather information through the display unit 351. In this case, one example of the prescribed command may include an input of making a fist twice. According to the example shown in FIG. 5B, the weather information is controlled to be outputted. For another example, another information (e.g., a schedule information, etc.), which is previously set by a user or a manufacturer, may be outputted.

Meanwhile, referring to FIG. 5A, if an input of making a fist twice is received, the mobile terminal 300 of the watch type is able to output a function guide popup window 500 including a guide that the weather information can be checked.

On the other hand, if the weather information displayed in FIG. 5B or the like is displayed over a prescribed time, it is able to automatically return to a normal state (e.g., a state of displaying a current hour, the state shown in FIG. 5A, etc.). Alternatively, it is able to return to the normal state in response to a reception of a return command (e.g., a palm input).

According to another embodiment of the present invention, if a user awakes from the sleep state, it is proposed to output a notification screen 501 for the cumulative notifications (or a notification list of a plurality of notifications) to the user [FIG. 5B]. The reason for this is that these notifications are saved without being outputted. After detecting that the user has got out of the sleep state, if a prescribed user command is received, the controller 180 can output a notification screen 501 for the cumulative notifications. In this case, one example of the prescribed command may include an input of making a fist twice.

According to the embodiment described in detail with reference to FIG. 5, a user's sleep state is determined based on a detected heart rate. According to another embodiment of the present invention, it is proposed to determine an exercising state of a user based on a heart rate. And, it is also proposed to run an appropriate function based on a result of the determination.

FIGS. 6A, 6B, 6C, 7A, 7B and 7C are diagrams for a control method of determining that a user is in a sleep state based on a heart rate and then running a function based on a result of the determination according to one embodiment of the present invention.

As mentioned in the foregoing description, a heart rate in an exercising state is higher than that in a normal state in general. Hence, if a heart rate per unit time is equal to or greater than a prescribed reference, the controller 180 may be able to determine that a user is in an exercising state.

In FIG. 6A, the controller 180 is assumed as determining that a user is in an exercising state as a result from detecting a heart rate of the user using the aforementioned method. If it is determined that the user is in the exercising state, the controller 180 can control a generated notification not to be outputted to the user. The reason for this is that the output of the notification may interrupt the user's exercise. The notification failing to be outputted is saved in turn. After the user finishes the exercise, the user can be informed of the saved notifications in a manner that the saved notifications are outputted [FIG. 6C].

According to one embodiment of the present invention, after an exercise has been finished, it is proposed to output an exercise summary information to the user [FIG. 6B]. The reason for this is that the summarized information 601 of the exercise is most useful information after finishing the exercise. After detecting that the user has finished the exercise, the controller 180 can output the summarized information 601 of the exercise through the display unit 351. In this case, one example of the prescribed command may include an input of making a fist twice. Moreover, the controller 180 may output a text 600 for querying whether to save an exercise record. If 'Yes (Y)' is selected, the controller 180 can control the corresponding exercise record to be saved.

According to one embodiment of the present invention, it is proposed to use a detected blood flow rate and/or a detected heart rate for the detection of the end of the exercise. According to the above-described embodiment, when an exercising state is determined, if a heart rate is equal to or greater than a prescribed reference, it is determined as the exercising state. Thus, if a detected heart rate becomes smaller than the prescribed reference, the controller 180 can determine that the exercising state is ended.

The summarized information 601 of the exercise may include at least one of a consumed calorie amount, a moving distance and a consumed time for the exercise. The summarized information 601 of the exercise shown in FIG. 6 is just one example, by which the present embodiment is non-limited.

According to another embodiment of the present invention, if it is detected that an exercising state is ended, it is proposed to output a notification screen 501 for cumulative notifications (or a notification list of a plurality of notifications) to a user [FIG. 6B]. The reason for this is that the notifications are saved instead of being outputted. If it is detected that the exercising state is ended, the controller 180 can output the notification screen 501 for the cumulative notifications through the display unit 351.

On the other hand, if the information displayed in FIG. 6B or the like is displayed over a prescribed time, it is able to automatically return to a normal state (e.g., a state of displaying a current hour, the state shown in FIG. 5A, etc.). Alternatively, it is able to return to the normal state in response to a reception of a return command (e.g., a palm input).

Meanwhile, it is difficult to clearly detect a timing point of getting out of the sleep state. The reason for this is that it takes a prescribed time for a heart rate to return to a normal level despite that a user awakes. Hence, according to one embodiment of the present invention, if a user command (e.g., a fist state is consecutively detected twice) indicating that a user gets out of a sleep state is received, it is able to control a prescribed function to be run.

On the other hand, since it takes a relatively short time for a heart rate to return to a normal state from an exercising state, a prescribed function can be run without a separate user command [cf. FIGS. 6A, 6B and 6C], by which the present embodiment is non-limited. For instance, a prescribed function may be run in response to a user command.

As mentioned in the foregoing description with reference to FIG. 5, if an input of making a fist twice is received, the mobile terminal 300 of the watch type is able to output a command guide popup window 500 for outputting a guide that the exercise summary information can be checked.

According to one embodiment of the present invention, proposed is a control method for displaying the summary information 601 while a user is exercising. Such an embodiment shall be described in detail with reference to FIGS. 7A, 7B and 7C as follows.

In the embodiment shown in FIGS. 7A, 7B and 7C, assume that the controller 180 determines that a user is in an exercising state based on a heart rate. And, it is proposed that the controller 180 outputs a summary information 601 on an exercise in response to a reception of a prescribed command during the exercising state.

In this case, the controller 180 classifies the summary information 601 into several items and is then able to control the classified items to be sequentially displayed in response to a reception of a prescribed command.

According to the example shown in FIGS. 7A, 7B and 7C, the summary information 601 is classified into a blood pressure information 701-1, an exercise schedule information 701-2 and a heart rate information 701-3. In particular, if a fist input is sequentially received during an exercising state, the controller 180 can sequentially output the classified summary informations 701-1 to 701-3.

Moreover, according to one embodiment of the present invention related to FIG. 7, in response to a reception of a return command, the display of the summary information 601 is stopped and a normal state (e.g., a state of turning off a power of a touchscreen, a state of displaying a current hour, etc.) can be restored. In this case, one example of the return command may include a palm input.

Meanwhile, according to one embodiment of the present invention, while a display unit 351 of a mobile terminal 300 of a watch type is turned off, a control method of turning on the display unit 351 or running a prescribed function is proposed. Such an embodiment is described in detail with reference to FIGS. 8A, 8B and 8C as follows.

FIGS. 8A, 8B and 8C are diagrams for a control method of activating a display unit or running a prescribed function by detecting a finger folded level according to one embodiment of the present invention.

According to the example shown in FIG. 8A, an operating state of the mobile terminal 300 of the watch type is a standby mode. In the standby mode, the controller 180 can deactivate the display unit 351. While the display unit 351 is in the deactivated state, if a prescribed command is received, the controller 180 may activate the display unit 351 [FIG. 8B] or may directly enter a home screen 800 after activating the display unit 351. The home screen 800 is further described as follows.

First of all, the home screen 800 may be generally defined as a screen initially displayed on the touchscreen 151 when a locked state of the touchscreen 151 is released. At least one icon or widget for running an application or an internal function may be displayed on the home screen 800. Optionally, at least two home screens 800 may exist in the mobile terminal 100. In this case, when a prescribed touch gesture is performed on the touchscreen 151, the at least two home screens 800 may sequentially displayed one by one. Different icons (widgets) may be disposed on the home screens 800, respectively.

Referring to FIG. 8C, in case that the home screen 800 is directly entered, it may be limited to a case that a password for the security is not set at the mobile terminal 300 of the watch type. According to one embodiment of the present invention, if a password is set, the controller 180 may output a screen for requesting activation of the display unit 351 and a password input without outputting the home screen 800 in direct.

Moreover, it may be able to distinguish an entry into the state shown in FIG. 8B from an entry into the state shown in FIG. 8C depending on a user command. In particular, if a folding input is received for a prescribed time (e.g., 3 seconds), the controller 180 can activate the display unit 351 as shown in FIG. 8B. If a fist input is received for a prescribed time (e.g., 3 seconds), the controller 180 can activate the display unit 351 and enter and output the home screen 800 as shown in FIG. 8C. In addition, if it is detected that the folding input is changed into the fist input, the controller 180 may control the state shown in FIG. 8B to be sequentially change into the state shown in FIG. 8C.

FIGS. 9A, 9B and 9C are diagrams for a control method of controlling an alarm based on a finger folded level in the course of outputting the alarm according to one embodiment of the present invention.

Referring to FIG. 9A, the mobile terminal 300 of the watch type is outputting an alarm set for 9 PM. The output of the alarm may include at least one of an output of an alarm screen 901 and an output of an alarm sound.

If a prescribed command is received during the alarm output, the controller 180 may stop/snooze the alarm output 902. According to the example shown in FIGS. 9A, 9B and 9C, the prescribed command may include a fist input.

While the fist input is received, if the fist input is switched to a folding input by unfolding fingers, the controller 180 may output a schedule notification 903 and 904. In particular, the schedule notification may include a schedule notification screen 903 and a voice guide 904 for the schedule.

According to the embodiment described with reference to FIGS. 9A, 9B and 9C, a user can easily control an alarm output in a manner of unfolding and folding fingers and is also able to access the schedule information easily.

A method of controlling a video recording state by an input of folding fingers is proposed with reference to FIGS. 10A, 10B, and 10C as follows.

FIGS. 10A, 10B, and 10C are diagrams for a control method of controlling a video recording state according to one embodiment of the present invention.

In FIG. 10, assume that a mobile terminal 100 shown in the drawing is connected to the mobile terminal 300 of the watch type according to one embodiment of the present invention by a short range communication or the like.

Assume that the state shown in FIG. 10A is a state of recording a video through the activated camera 121 of the mobile terminal 100. In the drawing, a preview 1001 of a screen currently recorded through the activated camera 121 is displayed through the display 151 of the mobile terminal 100.

If it is detected that an input of folding user's fingers is switched to a palm input through the mobile terminal 300 of the watch type, a control signal for ending the recording can be transmitted to the mobile terminal 100 [FIG. 10B]. Having received the control signal for ending the recording, the mobile terminal 100 stops the recording in progress and is able to save the recorded video.

If it is detected that an input of folding user's fingers is switched to a fist input through the mobile terminal 300 of the watch type, a control signal for capturing a screen can be transmitted to the mobile terminal 100 [FIG. 10C]. Having received the control signal for capturing the screen, the mobile terminal 100 captures a recorded screen and is able to save the captured screen.

Meanwhile, according to one embodiment of the present invention, further proposed is a method of controlling the mobile terminal 300 of the watch type during a call using a finger folded level. Such an embodiment is described in detail with reference to FIGS. 11A, 11B, 11C, 12A, 12B, 12C, 13A, 13B and 13C as follows.

FIGS. 11A, 11B and 11C are diagrams for a control method of detecting a finger folded level and then responding to a call signal using a result of the detection according to one embodiment of the present invention.

Referring to FIG. 11A, assume that a call signal is currently received through the mobile terminal 300 of the watch type. Through the display unit 351 shown in FIG. 11A, a call receiving screen 1101 indicating that the call signal is being received is currently displayed. In particular, the call receiving screen 1101 further includes a response icon 1102 for making a response to the received call signal. The mobile terminal 300 of the watch type is able to respond to the call signal in response to a prescribed touch gesture 10a applied to the response icon 1102.

According to one embodiment of the present invention, proposed is a control method of responding to a call signal based on a finger folded level as well as on a touch gesture applied to the response icon 1102.

According to the example shown in FIGS. 11A, 11B and 11C, in a situation that a call signal is currently received, if a fist input is maintained over a prescribed time (e.g., 3 seconds), the mobile terminal 300 of the watch type is able to make a response to the call signal [FIG. 11B]. Referring to FIG. 11B, the mobile terminal 300 of the watch type currently outputs a call connected screen 1103.

Moreover, according to one embodiment of the present invention, if a call is connected in response to a call signal, it is proposed that the call is ended based on an input of folding fingers.

While a call is connected, if a palm input is maintained over a prescribed time (e.g., 3 seconds) [FIG. 11B], the mobile terminal 300 of the watch type is able to end the connected call [FIG. 11C].

FIGS. 12A, 12B and 12C are diagrams for a control method of controlling a start/end of a recording in the course of a call based on a finger folded level according to one embodiment of the present invention.

Referring to FIG. 12A, if a recording start command is received during an output of the call connected screen 1103 described with reference to FIG. 11, it is able to start the recording of the connected call. In this case, the recording start command may include a gesture of switching a folding input to a fist input. Subsequently, referring to FIG. 12B, the mobile terminal 300 of the watch type is able to output a recording progress screen 1201 for displaying that the recording is in progress.

After the recording has been started, if a recording end command is received during the recording, the mobile terminal 300 of the watch type ends the recording and is able to save the recorded audio information. In this case, as shown in FIGS. 12A, 12B and 12C, the recording end command may include a gesture of switching a fist input to a folding input.

FIGS. 13A, 13B and 13C are diagrams for a control method of controlling a call volume based on a folded level in the course of a call according to one embodiment of the present invention.

In FIGS. 13A, 13B and 13C, assume that a call is in progress. And, a call connected screen 1103 is outputted. Assume that a call volume shown in FIG. 13A is the lowest volume. Assume that a call volume shown in FIG. 13B is the intermediate volume. Assume that a call volume shown in FIG. 13C is the highest volume. If a command for raising a volume is received, the mobile terminal 300 of the watch type can control the call volume to be gradually raised [adjusted into FIG. 13C from FIG. 13A]. If a command for lowering a volume is received, the mobile terminal 300 of the watch type can control the call volume to be gradually lowered [adjusted into FIG. 13A from FIG. 13C].

According to one embodiment of the present invention, a command for raising a volume may include a gesture of switching to a palm input, a folding input and a fist input gradually [switching to FIG. 13C from FIG. 13A]. According to one embodiment of the present invention, a command for lowering a volume may include a gesture of switching to a fist input, a folding input and a palm input gradually [switching to FIG. 13A from FIG. 13C.]

In a stopwatch controlling method, it is able to use a detection of an action of folding fingers. Such an embodiment is described in detail with reference to FIGS. 14A, 14B and 14C and FIGS. 15A, 15B and 15C as follows.

Figure 14A:
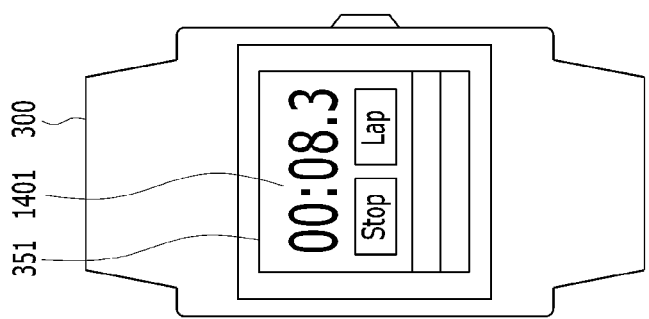
FIGS. 14A, 14B and 14C are diagrams for a control method of controlling a start/end of a stopwatch based on a motion of folding fingers according to one embodiment of the present invention.
Figure 14B:
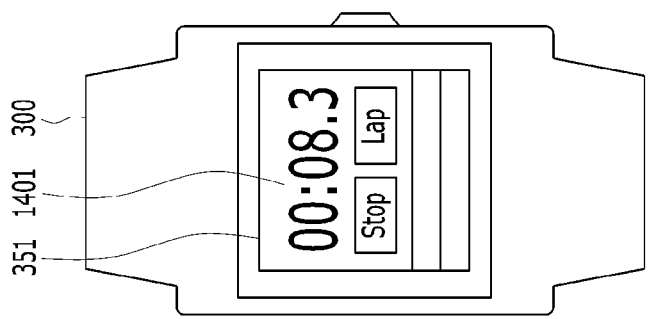
Figure 14C:
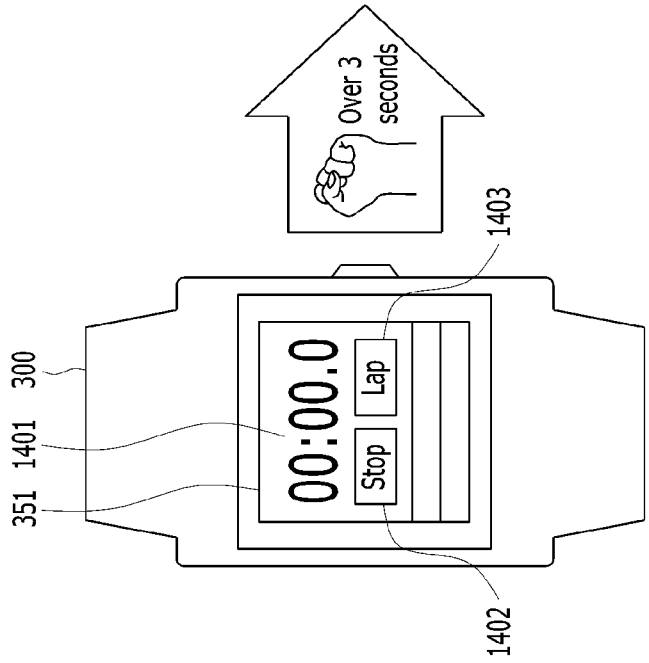

FIGS. 14A, 14B and 14C are diagrams for a control method of controlling a start/end of a stopwatch based on a motion of folding fingers according to one embodiment of the present invention.

Referring to 14A, 14B and 14C, the mobile terminal 300 of the watch type is outputting a running screen 1401 of a stopwatch. In this case, the running screen 1401 may include a start/end button 1402 and a lap time button 1403 for recording a lap time.

If a start command is received, referring to FIG. 14B, the mobile terminal 300 of the watch type is able to start the stopwatch. In this case, the start command may include an input of touching the start/end button 1402 in general. According to one embodiment of the present invention, one example of the start command may include a fist input maintained over a prescribed time.

If an end command is received, referring to FIG. 14C, the mobile terminal 300 of the watch type is able to end the stopwatch. Likewise, the end command may include an input of touching the start/end button 1402 in general. According to one embodiment of the present invention, one example of the end command may include a palm input maintained over a prescribed time.

According to one embodiment of the present invention, further proposed is a method of recording a lap time of a stopwatch as well as starting/ending the stopwatch.

Figure 15C:
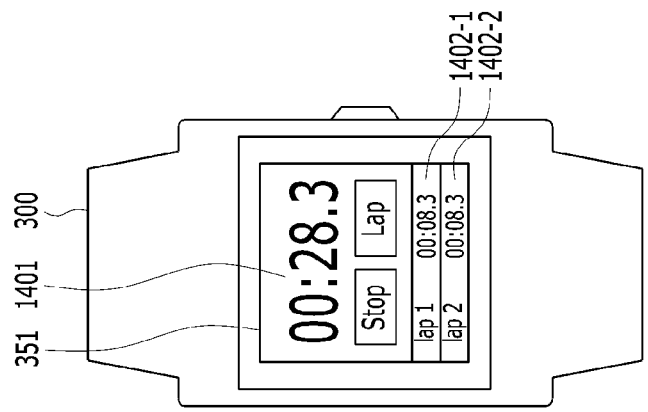
FIGS. 15A, 15B and 15C are diagrams for a control method of controlling a lap time of a stopwatch based on a motion of folding fingers according to one embodiment of the present invention.
Figure 15B:
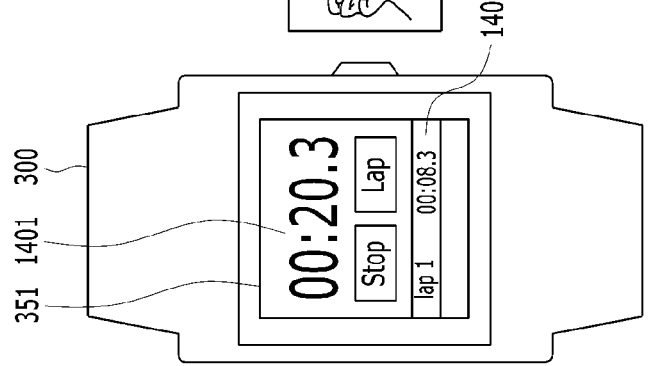
Figure 15A:
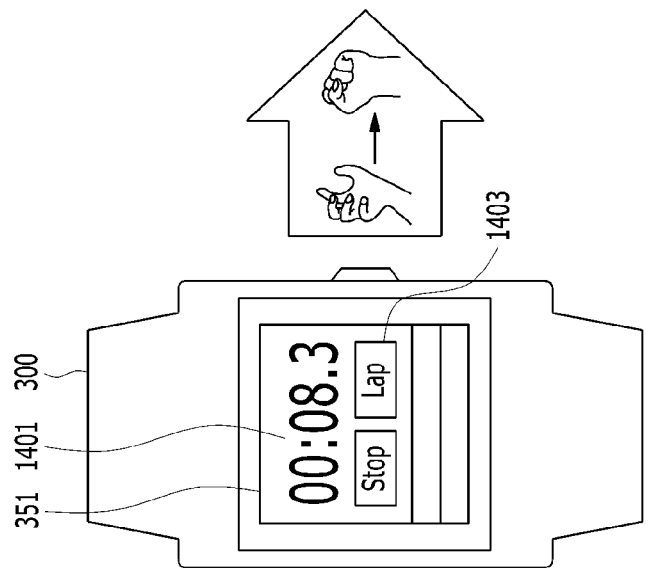

FIGS. 15A, 15B and 15C are diagrams for a control method of controlling a lap time of a stopwatch based on a motion of folding fingers according to one embodiment of the present invention.

Referring to 15A, 15B and 15C, after a timer of a stopwatch has started, if a lap time button 1403 is selected, the mobile terminal 300 of the watch type saves a corresponding time as a lap time and is able to output the saved lap time. For instance, if an input of selecting the lap time button 1403 is received at 00:08.3, the controller 180 saves the corresponding time and is able to output a $1^{st}$ lap time 1402-1 to a running screen 1401.

According to one embodiment of the present invention, it is proposed to detect a finger folded level instead of applying an input of selecting the lap time button 1403. In particular, if it is detected that a folding input is switched to a fist input at a specific time, the mobile terminal 300 of the watch type is able to save the specific time as a lap time.

If a folding input is switched to a fist input at a time 00:08.3 in FIG. 15A, the mobile terminal 300 of the watch type saves the corresponding time 00:08.3 as a 1.sup.st lap time 1402-1 and is able to output it to the running screen 1401 [FIG. 15B].

Meanwhile, it is apparent to those skilled in the art that the recording of the lap time can be repeatedly performed. Hence, if a folding input is switched to a fist input at a time 00:20.3 in FIG. 15B, the mobile terminal 300 of the watch type saves the corresponding time 00:20.3 as a $2^{nd}$ lap time 1402-2 and is able to output it to the running screen 1401 together with the $1^{st}$ lap time 1402-1 [FIG. 15C].

Meanwhile, according to the above-described embodiment of the present invention, considered is the control method by detecting the level of folding fingers only. In the following description, a controlling method by further detecting an input of rotating a wrist together with a level of folding fingers is proposed.

FIGS. 16A, 16B and 16C are diagrams for a control method of detecting a finger folded level and an input of rotating a wrist and then reading a received text based on a result of the detection according to one embodiment of the present invention.

Referring to FIG. 16A, assume that the mobile terminal 300 of the watch type receives a text message. The mobile terminal 300 of the watch type outputs a notification screen 501 that notifies that there is a received text message.

If a message check command is received, referring to FIG. 16B, the controller 180 can output a message check screen 1601 for displaying details of the received text message. According to one embodiment of the present invention, one example of the message check command may include a folding input.

According to one embodiment of the present invention, a scroll action on the message check screen 1601 is proposed to be performed by a rotation of a wrist. In this case, the rotation of the wrist may include a rotation of a wrist on which the mobile terminal 300 of the watch type is worn. If the wrist is rotated in a $1^{st}$ direction, the mobile terminal 300 of the watch type can scroll to move the outputted message check screen 1601 [FIG. 16C].

The direction for rotating the wrist may include the scroll direction. In particular, if a scroll in a bottom direction is desired, it is able to rotate the wrist in the bottom direction (e.g., a bottom direction of eyes on watching the display unit 351).

Figure 17A:
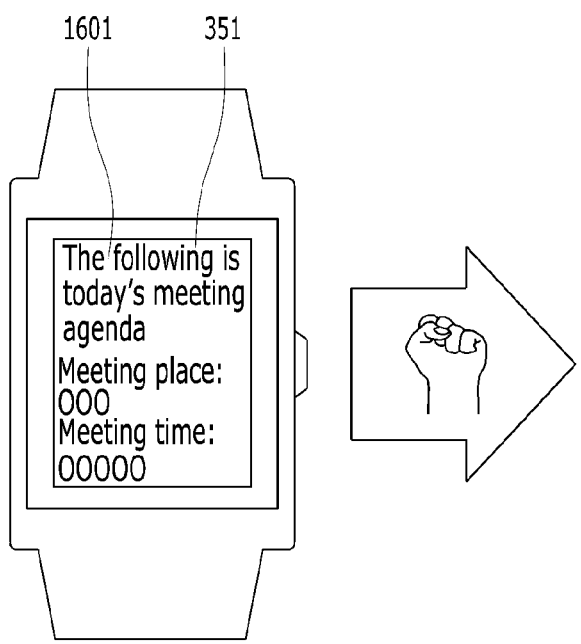
FIGS. 17A and 17B are diagrams for a control method of switching a message check screen 1601 to a lock screen according to one embodiment of the present invention.
Figure 17B:
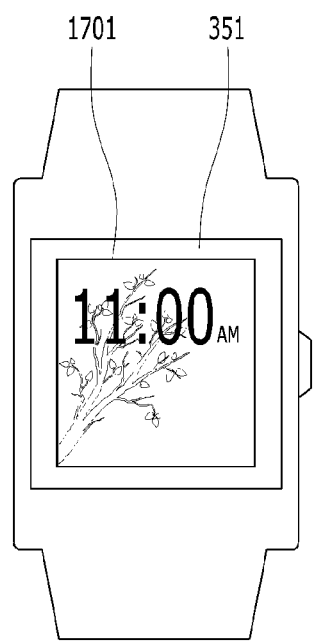

FIGS. 17A and 17B are diagrams for a control method of switching a message check screen 1601 to a lock screen according to one embodiment of the present invention.

Referring to FIG. 17A, as mentioned in the foregoing description with reference to FIGS. 16A, 16B and 16C, the message check screen 1601 is outputted through the display unit 351. If a command for switching to a lock screen is received, the controller 180 stops the output of the message check screen 101 and is able to output a lock screen 1701 through the display screen 351. In this case, one example of the command for switching to the lock screen may include a fist input.

In the following description, a method of controlling a gallery application in accordance with a finger folded level is described.

FIGS. 18A, 18B, 18C, 18D, 18E and 18F are diagrams for a control method of controlling a gallery application in proportion to a finger folded level according to one embodiment of the present invention.

Figure 18C:
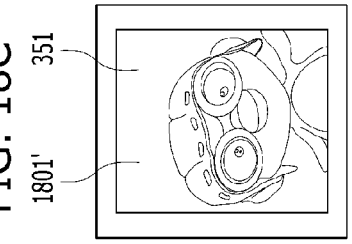
FIGS. 18A, 18B, 18C, 18D, 18E and 18F are diagrams for a control method of controlling a gallery application in proportion to a finger folded level according to one embodiment of the present invention.
Figure 18F:
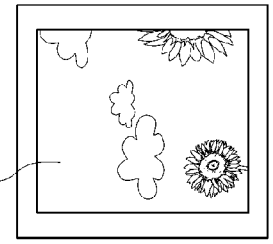
Figure 18B:
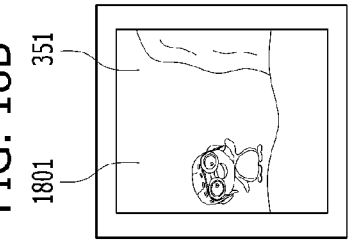
Figure 18E:
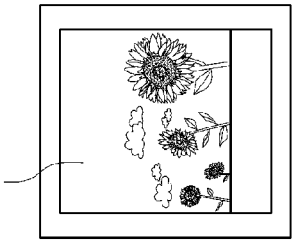

FIGS. 18A to 18F show a running screen of a gallery application. Referring to FIG. 18B, a $1^{st}$ image data 1801 is outputted through the running screen of the gallery application. If a photo switch command is received, the mobile terminal 300 of the watch type is able to switch the $1^{st}$ image data 1801 to a $2^{nd}$ image data 1803 [FIG. 18E]. In this case, the photo switch command may include a gesture of rotating the mobile terminal 300 of the watch type in a $1^{st}$ direction during a reception of a folding input.

If an image enlargement command is received, the mobile terminal 300 of the watch type is able to enlarge and display the currently displayed image data. For instance, while the $1^{st}$ image data 1801 is outputted [FIG. 18B], if the image enlargement command is received, the mobile terminal 300 of the watch type is able to output an enlarged screen 1801' of the $1^{st}$ image data [FIG. 18C].

Likewise, if an image reduction command is received, the mobile terminal 300 of the watch type is able to reduce and display the currently displayed image data. For instance, while the $1^{st}$ image data 1801 is outputted [FIG. 18B], if the image reduction command is received, the mobile terminal 300 of the watch type is able to output a reduced screen 1801' of the $1^{st}$ image data [FIG. 18A]. Meanwhile, while the $1^{st}$ image data is reduced to the maximum (i.e., a full region of the image data is displayed), if the image reduction command is received, the mobile terminal 300 of the watch type is able to output an image thumbnail list 1802 [FIG. 18D].

According to one embodiment of the present invention, the image enlargement command may include a gesture of switching a folding input to a palm input, while the image reduction command may include a gesture of switching a folding input to a fist input.

Figure 18A:
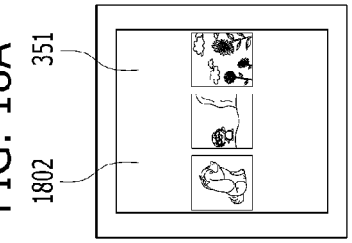
Figure 18D:
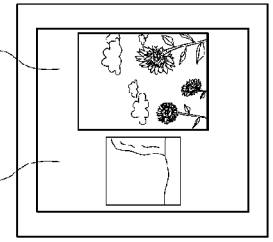

Meanwhile, the above-described photo switch command may be applicable to the enlarged state, the reduced state, or the image thumbnail state. In particular, if the photo switch command is received during the output of the enlarged screen 1801' of the $1^{st}$ image, it may be able to switch to the enlarged screen 1803' of the $2^{nd}$ image [i.e., switched to FIG. 18F from FIG. 18C]. Moreover, while the image thumbnail list shown in FIG. 18A is outputted with reference to the $1^{st}$ image, if the photo switch command is received, it may be able to switch to the image thumbnail list shown in FIG. 18D with reference to the $2^{nd}$ image.

The above-described embodiment relates to the method of controlling the mobile terminal 300 of the watch type itself. According to embodiments of the present invention mentioned in the following description, proposed is a control method for controlling another external mobile terminal 100 connected to the mobile terminal 300 of the watch type by a short range communication and/or the like. In particular, if a user's command is received, the mobile terminal 300 of the watch type transmits a control signal to the mobile terminal 100 using the short range communication or the like. Having received the control signal, the mobile terminal 100 is able to run a corresponding function. In particular, it is able to control another mobile terminal 100 using the finger folded input for facilitating the control of the mobile terminal 300 of the watch type extensively. In the following description, the control of the mobile terminal 100 may relate to the control of the mobile terminal 100 connected to the mobile terminal 300 of the watch type by a short range communication or the like.

According to one embodiment of the present invention, further proposed is a user command for controlling a photographing. Such an embodiment is described in detail with reference to FIGS. 19A, 19B and 19C as follows.

FIGS. 19A, 19B and 19C are diagrams for a control method of taking a photo through an activated camera by detecting a finger folded level according to one embodiment of the present invention.

Referring to FIG. 19A, a preview screen 1901 for an image received through an activated camera is currently outputted. If a focus adjust command is received, the mobile terminal 300 of the watch type is able to run an auto focus function [FIG. 19B]. In this case, one example of the auto focus function may include a folding input. And, a focus indicator 1902 corresponding to a focus obtained through the auto focus function can be displayed on the preview screen 1901 shown in FIG. 19B.

If a photograph command is received, it is able to take a photo through the activated camera 121 [FIG. 19C]. According to one embodiment of the present invention, the photograph command may include a fist input.

A control method in playing a video is described in detail with reference to FIGS. 20A, 20B, 20C, 21A, 21B and 21C as follows.

FIGS. 20A, 20B, 20C, 21A, 21B and 21C are diagrams for a control method of controlling volume/brightness of a video play by detecting a finger folded level according to one embodiment of the present invention.

Figure 20A:
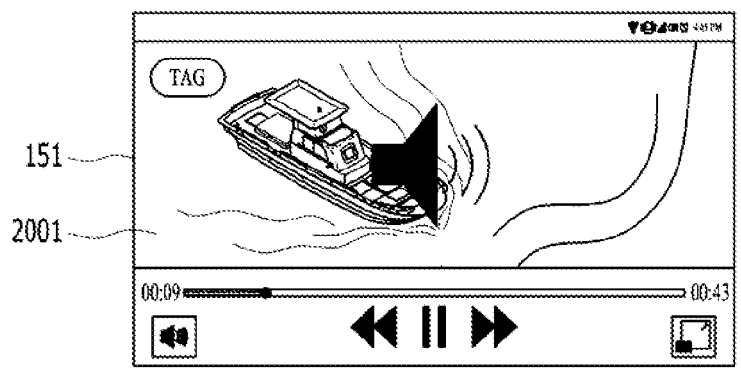
FIGS. 20A, 20B, 20C, 21A, 21B and 21C are diagrams for a control method of controlling volume/brightness of a video play by detecting a finger folded level according to one embodiment of the present invention.
Figure 20B:
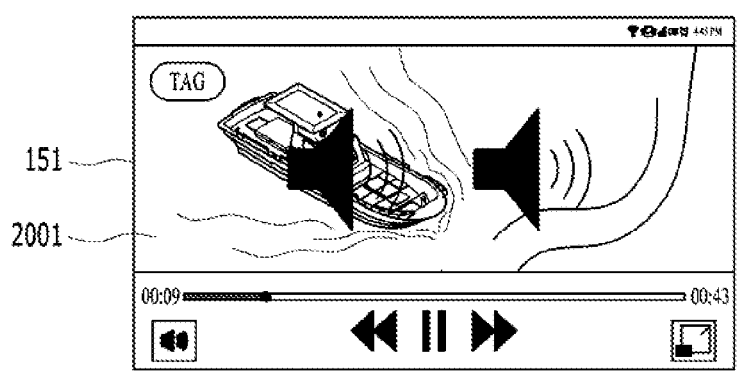
Figure 20C:
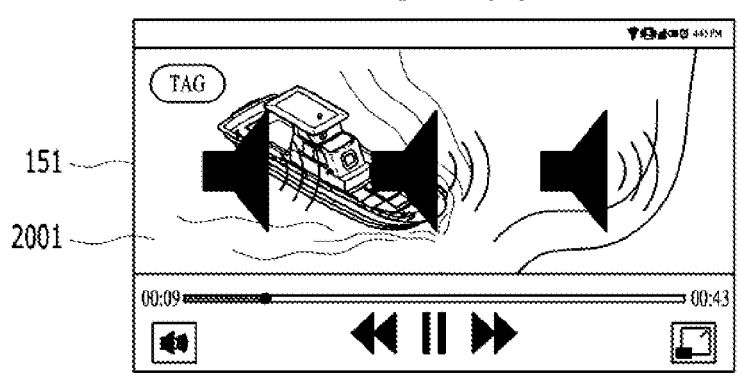

Referring to FIGS. 20A to 20C, a video play screen 2001 is currently displayed. If a command for raising a volume is received, the mobile terminal 300 of the watch type is able to control a video play volume to be gradually raised [adjusted to the state shown in FIG. 20C from the state shown in FIG. 20A]. If a command for lowering a volume is received, the mobile terminal 300 of the watch type is able to control a video play volume to be gradually lowered [adjusted to the state shown in FIG. 20A from the state shown in FIG. 20C].

According to one embodiment of the present invention, the command for raising the volume may include an input of rotating a hand in a $1^{st}$ direction while fingers are folded. And, the command for lowering the volume may include an input of rotating a hand in a $2^{nd}$ direction while fingers are folded.

Figure 21A:
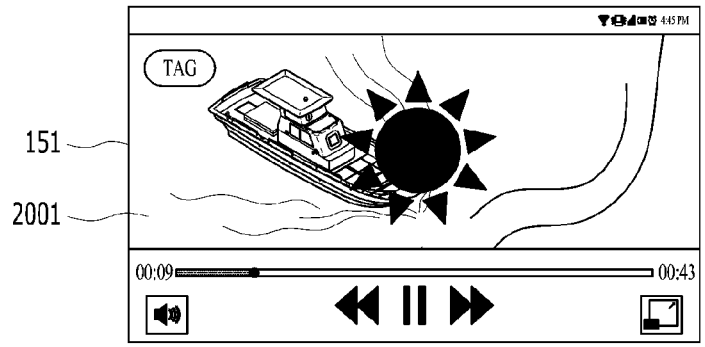
Figure 21B:
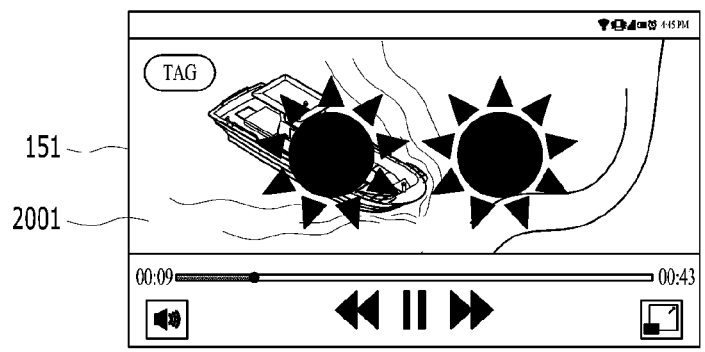
Figure 21C:
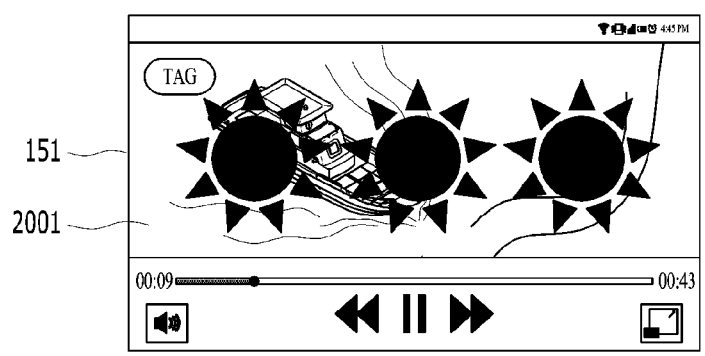

Likewise, referring to FIGS. 21A to 21C, a video play screen 2001 is currently displayed. If a command for raising a screen brightness is received, the mobile terminal 300 of the watch type is able to control the screen brightness to be gradually raised [adjusted to the state shown in FIG. 21C from the state shown in FIG. 21A]. If a command for lowering the screen brightness is received, the mobile terminal 300 of the watch type is able to control the screen brightness to be gradually lowered [adjusted to the state shown in FIG. 21A from the state shown in FIG. 21C].

According to one embodiment of the present invention, the command for raising the screen brightness may include an input of rotating a hand in a $1^{st}$ direction while a fist is made. And, the command for lowering the screen brightness may include an input of rotating a hand in a $2^{nd}$ direction while the fist is made.

According to one embodiment of the present invention, further proposed is a control method of activating a display of another mobile terminal 100 connected to the mobile terminal 300 of the watch type or releasing a locked display of the mobile terminal 100 through an action of knocking with a hand having the mobile terminal 300 of the watch type worn thereon. Such an embodiment is described in detail with reference to FIG. 22 as follows.

FIG. 22 is a diagram for a control method of unlocking a different mobile terminal 100 through an input of a knock with a hand having a watch type mobile terminal 300 worn thereon according to one embodiment of the present invention.

Referring to FIG. 22, if a result detected from at least one of the microphone, the acceleration sensor, the gyro sensor and the gravity sensor provided to the mobile terminal 300 of the watch type is analyzed, the mobile terminal 300 of the watch type may be able to detect a user's action of knocking on a floor or the like through a hand having the mobile terminal 300 of the watch type worn thereon. Moreover, the mobile terminal 300 of the watch type may be able to determine whether the knocking action is performed in a fist made state, a folding state, or a state of unfolding fingers all. In particular, the mobile terminal 300 of the watch type may be able to distinguish a palm knock from a fist knock. According to one embodiment of the present invention, a state on detecting the knock is detected and the detected state is used as a knock code for releasing a lock screen of another mobile terminal 100.

In this case, assume that the mobile terminal 300 of the watch type and another mobile terminal 100 are connected to each other by a short range communication and/or the like.

For instance, in case that a $1^{st}$ knock code 2201a is preset as an unlock code, if a fist knock, a palm knock, a fist knock and a palm knock are sequentially detected, the mobile terminal 100 releases the lock and is able to output a home screen 2202.

Meanwhile, an input for designating a timing point of ending an input of the knock code is further proposed. A length of the knock code may include a specified length or may be set different per user. Since the length of the knock code can enhance security, an input for designating an end point of a knock code is proposed. According to the above example, after the $1^{st}$ knock code 2201a has been inputted, if a code input complete command is received, the mobile terminal 300 of the watch type is able to output the home screen 2202. According to the example shown in FIG. 22, the code input complete command may include an input of swaying a hand having the mobile terminal 300 of the watch type worn thereon horizontally by unfolding fingers of the hand.

The $1^{st}$ knock code 2201a is just one example and various knock codes 2201b, 201c . . . can be set as unlock codes.

Meanwhile, a control method of assisting a proximity touch using a finger folded level is further proposed. Such an embodiment is described in detail with reference to FIGS. 23A to 25B as follows.

Figure 23C:
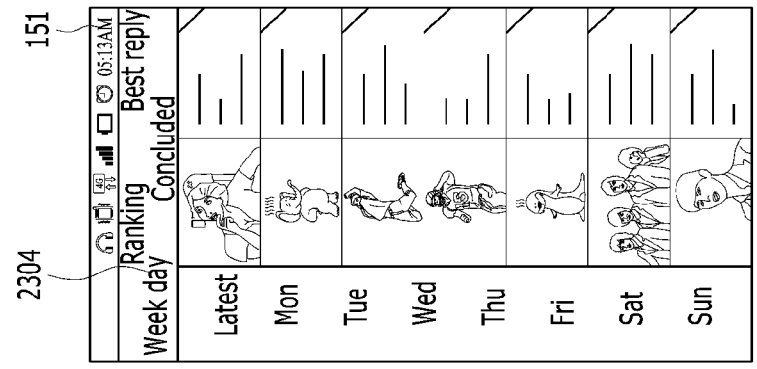
FIGS. 23A, 23B and 23C are diagrams for a control method of assisting a proximity touch based on a finger folded level according to one embodiment of the present invention.
Figure 23B:
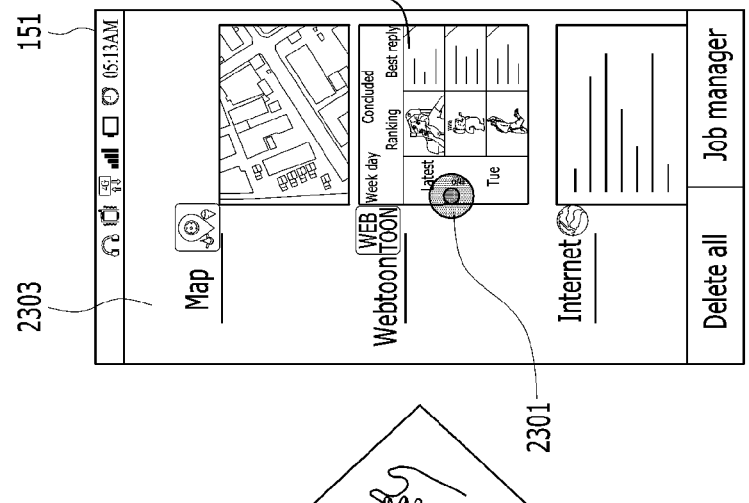
Figure 23A:
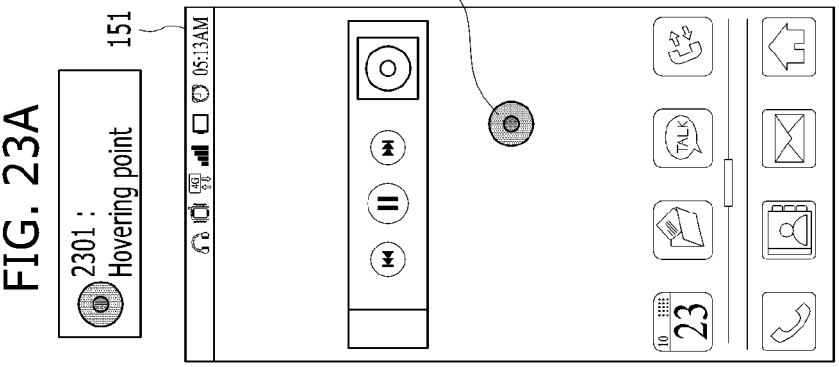

FIGS. 23A, 23B and 23C are diagrams for a control method of assisting a proximity touch based on a finger folded level according to one embodiment of the present invention.

Referring to FIG. 23, a proximity touch may mean an input of approaching close to the touchscreen 151 in a prescribed distance instead of directly touching a surface of the touchscreen 151 of the mobile terminal 100 with a touch tool (e.g., a finger, a touch pen, etc.). Like a direct touch, the proximity touch can specify a location of the touchscreen 151. For instance, the touch tool may be able to specify a location closest to the touchscreen 151. Such a specified location shall be named a hovering point 2301 shown in FIG. 23.

Referring to FIG. 23A, a home screen is currently displayed on the touchscreen 151 of the mobile terminal 100. And, a hovering point 2301 is displayed by a proximity touch. In this case, the mobile terminal 100 may be currently connected to the mobile terminal 300 of the watch type according to one embodiment of the present invention.

According to one embodiment of the present invention, if a prescribed command is received through the mobile terminal 300 of the watch type, the mobile terminal 300 of the watch type is able to output a recently run application list 2303. On example of the prescribed command received through the mobile terminal 300 of the watch type according to one embodiment of the present invention may include a folding input with a hand having the mobile terminal 300 of the watch type worn thereon.

If a prescribed item is selected from the recently run application list 2303, the mobile terminal 100 runs an application mapped to the selected item and is able to output a running screen of the run application [FIG. 23C]. Meanwhile, the input of selecting the prescribed item may include an input of directly touching the corresponding item on the touchscreen 151. Moreover, according to one embodiment of the present invention, the selecting input may include an input performed in a manner of locating a hovering point 2301 on an item to be selected and then making a fist. In particular, while the mobile terminal 100 detects a proximity touch, if an input of making a fist is detected through the mobile terminal 300 of the watch type, the mobile terminal 100 is able to select the item corresponding to the proximity touch.

According to the above-described embodiment, an operation of selecting a prescribed item from an application list is taken as one example. Yet, it is apparent to those skilled in the art that the above-described embodiment is applicable to various cases of making a selection from a screen.

Meanwhile, in case that a screen is displayed through two layers, a method of controlling each of the layers is proposed. Such an embodiment is described in detail with reference to FIGS. 24A, 24B, 25A and 25B as follows.

FIGS. 24A, 24B, 25A and 25B are diagrams for a control method of controlling a screen displayed through two layers according to one embodiment of the present invention.

Referring to FIG. 24A to FIG. 25B, the mobile terminal 100 is outputting a home screen through a $1^{st}$ layer 2401 and is also outputting a webpage through a $2^{nd}$ layer 2402.

According to one embodiment of the present invention, as an input for switching the $1^{st}$ layer 2401, proposed is an input 10c of swiping right and left by unfolding fingers all. In particular, if a command for switching the $1^{st}$ layer 2401 is received, the mobile terminal 100 is able to switch the home screen 2202 to another screen 2202'.

In this case, the swiping may mean an input of moving a touch tool (e.g., a hand, etc.) in a left to right direction or a right to left direction by locating the touch tool proximate to the touchscreen 151.

According to one embodiment of the present invention, as an input for switching the $2^{nd}$ layer 2402, an input 10d of swiping left to right by making a fist is proposed. In particular, if a command for switching the $2^{nd}$ layer 2402 is received, the mobile terminal 100 is able to switch the webpage 2403 to another screen 2403'. Meanwhile, the input for switching the $1^{st}$ layer and the input for switching the $2^{nd}$ layer are exemplary only. And, it is apparent that the input for switching the $1^{st}$ layer and the input for switching the $2^{nd}$ layer may be applicable by being switched to each other.

Various embodiments may be implemented using a machine-readable medium having instructions stored thereon for execution by a processor to perform various methods presented herein. Examples of possible machine-readable mediums include HDD (Hard Disk Drive), SSD (Solid State Disk), SDD (Silicon Disk Drive), ROM, RAM, CD-ROM, a magnetic tape, a floppy disk, an optical data storage device, the other types of storage mediums presented herein, and combinations thereof. If desired, the machine-readable medium may be realized in the form of a carrier wave (for example, a transmission over the Internet). The processor may include the controller 180 of the mobile terminal.

The foregoing embodiments are merely exemplary and are not to be considered as limiting the present disclosure. The present teachings can be readily applied to other types of methods and apparatuses. This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments.

As the present features may be embodied in several forms without departing from the characteristics thereof, it should also be understood that the above-described embodiments are not limited by any of the details of the foregoing description, unless otherwise specified, but rather should be considered broadly within its scope as defined in the appended claims, and therefore all changes and modifications that fall within the metes and bounds of the claims, or equivalents of such metes and bounds, are therefore intended to be embraced by the appended claims.

What is claimed is:

1. A wearable mobile terminal comprising:
a display;
a sensing unit configured to measure a blood flow rate at a wrist of a user wearing the wearable mobile terminal; and
a controller configured to:
execute a first function and cause the display to display a screen corresponding to the first function when a state of fingers of the user is changed from a completely unfolded state to a fist state such that a variation of the measured blood flow rate meets or exceeds a first threshold value; and
execute a second function and cause the display to display a screen corresponding to the second function that is different than the first function when the state of fingers of the user is changed from the fist state to the completely unfolded state such that the variation of the measured blood flow rate meets or exceeds a second threshold value,
wherein the state of fingers of the user is determined as the completely unfolded state or the fist state based on the variation of the measured blood flow rate.

2. The mobile terminal of claim 1, wherein:
the controller is further configured to determine whether an activity state of the user is a sleep state or an exercising state based on the measured blood flow rate; and
the first or second function corresponds to the determined state of fingers and the determined activity state.

3. The mobile terminal of claim 2, wherein the controller is further configured to:
detect a heart rate of the user based on the measured blood flow rate to determine the activity state of the user; and
determine the activity state as the exercising state when the detected heart rate is equal to or greater than a prescribed numerical value.

4. The mobile terminal of claim 2, wherein the controller is further configured to:
detect a heart rate of the user based on the measured blood flow rate to determine the activity state of the user; and
determine the activity state as the sleep state when the detected heart rate is less than a prescribed numerical value.

5. The mobile terminal of claim 2, wherein the screen corresponding to the first or second function comprises exercise summary information when the activity state is determined as the exercising state.

6. The mobile terminal of claim 2, wherein:
the controller is further configured to cause the display to display a first notification in response to a first prescribed event that occurs while the determined activity state is not the sleep state or exercising state; and
when a second prescribed event occurs while the determined activity state is the sleep state or exercising state, a second notification corresponding to the second prescribed event is not displayed until the activity state is determined to be a state other than the sleep state or exercising state.

7. The mobile terminal of claim 6, further comprising a memory, wherein the controller is further configured to:
cause the memory to store the second notification when the measured blood flow is determined to be in a first range such that the activity state is determined to be the sleep state or exercising state; and
cause the display to display the stored second notification when the measured blood flow is determined to be in a second range such that the activity state is determined to be the state other than the sleep state or exercising state.

8. The mobile terminal of claim 1, wherein the controller is further configured to cause the display to display the screen corresponding to the first or second function based on the variation of the measured blood flow rate without requiring a user input.

9. The mobile terminal of claim 1, further comprising a wireless communication unit, wherein the first or second function comprises a function of responding to a call signal received via the wireless communication unit.

10. A method for controlling a wearable mobile terminal, the method comprising:
measuring a blood flow rate at a wrist of a user wearing the wearable mobile terminal;
executing a first function and displaying a screen corresponding to the first function when a state of fingers of the user is changed from a completely unfolded state to a fist state such that a variation of the measured blood flow rate meets or exceeds a first threshold value; and executing a second function and displaying a screen corresponding to the second function that is different than the first function when the state of fingers of the user is changed from the fist state to the completely unfolded state such that the variation of the measured blood flow rate meets or exceeds a second threshold value, wherein the state of fingers of the user is determined as the completely unfolded state or the fist state based on the variation of the measured blood flow rate.

11. The method of claim 10, further comprising determining whether an activity state of the user is a sleep state or an exercising state based on the measured blood flow rate, wherein the first or second function corresponds to the determined state of fingers and the determined activity state.

12. The method of claim 11, wherein the determining the activity state comprises:
   detecting a heart rate of the user based on the measured blood flow rate; and
   determining the activity state as the exercising state when the detected heart rate is equal to or greater than a prescribed numerical value.

13. The method of claim 11, wherein the determining the activity state comprises:
   detecting a heart rate of the user based on the measured blood flow rate; and
   determining the activity state as the sleep state when the detected heart rate is less than a prescribed numerical value.

14. The method of claim 11, wherein the screen corresponding to the first or second function comprises exercise summary information when the activity state is determined as the exercising state.

15. The method of claim 11, further comprising displaying a first notification in response to a first prescribed event that occurs while the determined activity state is not the sleep state or exercising state, wherein when a second prescribed event occurs while the determined activity state is the sleep state or exercising state, a second notification corresponding to the second prescribed event is not displayed until the activity state is determined to be a state other than the sleep state or exercising state.

16. The method of claim 15, further comprising:
   storing the second notification in a memory when the measured blood flow is determined to be in a first range such that the activity state is determined to be the sleep state or exercising state; and
   displaying the stored second notification when the measured blood flow is determined to be in a second range such that the activity state is determined to be the state other than the sleep state or exercising state.

17. The method of claim 10, wherein the screen corresponding to the first or second function is displayed based on the variation of the measured blood flow rate without requiring a user input.

18. The method of claim 10, wherein the first or second function comprises a function of responding to a call signal received via a wireless communication unit.

* * * * *